(12) United States Patent
Okawa et al.

(10) Patent No.: US 10,033,258 B2
(45) Date of Patent: Jul. 24, 2018

(54) LINEAR ACTUATOR, ELECTRIC BRUSH, ELECTRIC CUTTING MACHINE AND ELECTRIC AIR PUMP

(71) Applicants: Tatsunori Okawa, Tokyo (JP); Yuki Takahashi, Tokyo (JP); Chikara Sekiguchi, Tokyo (JP); Shigenori Inamoto, Tokyo (JP)

(72) Inventors: Tatsunori Okawa, Tokyo (JP); Yuki Takahashi, Tokyo (JP); Chikara Sekiguchi, Tokyo (JP); Shigenori Inamoto, Tokyo (JP)

(73) Assignee: MITSUMI ELECTRIC CO., LTD., Tokyo (JP)

( * ) Notice: Subject to any disclaimer, the term of this patent is extended or adjusted under 35 U.S.C. 154(b) by 318 days.

(21) Appl. No.: 14/868,775

(22) Filed: Sep. 29, 2015

(65) Prior Publication Data

US 2016/0094115 A1 Mar. 31, 2016

(30) Foreign Application Priority Data

Sep. 30, 2014 (JP) .................................. 2014-201783

(51) Int. Cl.
*H02K 33/16* (2006.01)
*A61C 17/34* (2006.01)

(52) U.S. Cl.
CPC ......... *H02K 33/16* (2013.01); *A61C 17/3445* (2013.01)

(58) Field of Classification Search
CPC .......................................... H02K 33/00–33/18

(Continued)

(56) References Cited

U.S. PATENT DOCUMENTS 5,189,751 A * 3/1993 Giuliani ................. A61C 17/20
15/22.1
6,652,252 B2 * 11/2003 Zabar .................... F04B 35/045
310/12.21

(Continued)

FOREIGN PATENT DOCUMENTS

EP    1626483 A1    2/2006
EP    2374430 A1    10/2011

(Continued)

OTHER PUBLICATIONS

Extended European Search Report for EP 15187413.8 dated Mar. 3, 2016.

*Primary Examiner* — Thomas Truong
(74) *Attorney, Agent, or Firm* — Brundidge & Stanger, P.C.

(57) ABSTRACT

A linear actuator that can achieve downsizing with a simple configuration, and can provide stable linear reciprocation while achieving improvement in assemblability and cost reduction. In the actuator, movable member 50 faces coil 21 in the winding axis CL direction of coil 21, and in addition, includes magnet 30 magnetized in the coil-winding axis CL direction in a unipolar fashion and output shaft 60 extending in the CL direction. Elastic body 70 is disposed along the coil-winding axis CL direction and configured to deform in that direction to supports movable member 50 such that movable member 50 can reciprocate along the coil-winding axis CL direction. Elastic body 70 is fixed to fixing body 40 and movable member 50 at both ends 71 and 72 in the coil-winding axis CL direction such that central air gap CG is formed between electromagnet 20 and magnet 30.

15 Claims, 22 Drawing Sheets

(58) Field of Classification Search
USPC .................................................. 310/15–39
See application file for complete search history.

(56) References Cited

U.S. PATENT DOCUMENTS

| | | | | |
|---|---|---|---|---|
| 7,239,053 B2 * | 7/2007 | Brill | ................ | B26B 19/06 |
| | | | | 30/210 |
| 2003/0142845 A1 * | 7/2003 | Miyamoto | ............ | H02K 33/16 |
| | | | | 381/396 |
| 2004/0130221 A1 * | 7/2004 | Ichii | ................ | A61C 17/34 |
| | | | | 310/12.31 |
| 2006/0066154 A1 * | 3/2006 | Ogino | .................. | H02K 33/16 |
| | | | | 310/15 |
| 2006/0158048 A1 * | 7/2006 | Kobayashi | ......... | A61C 17/3445 |
| | | | | 310/12.04 |
| 2013/0313838 A1 * | 11/2013 | Sakamoto | ................ | F03G 7/08 |
| | | | | 290/1 R |
| 2014/0103750 A1 | 4/2014 | Ishihara et al. | | |

FOREIGN PATENT DOCUMENTS

| | | | |
|---|---|---|---|
| JP | 3475949 B2 | 12/2003 |
| JP | 2005-160134 A | 6/2005 |
| JP | 2006-325381 A | 11/2006 |
| JP | 2013-233537 A | 11/2013 |

\* cited by examiner

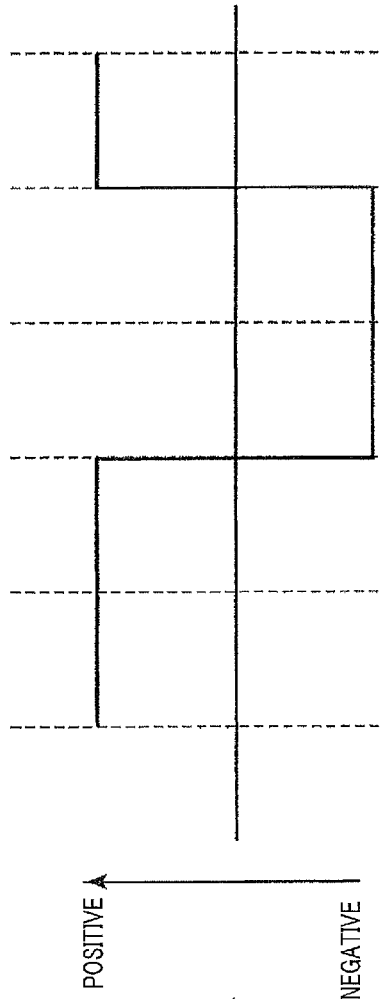
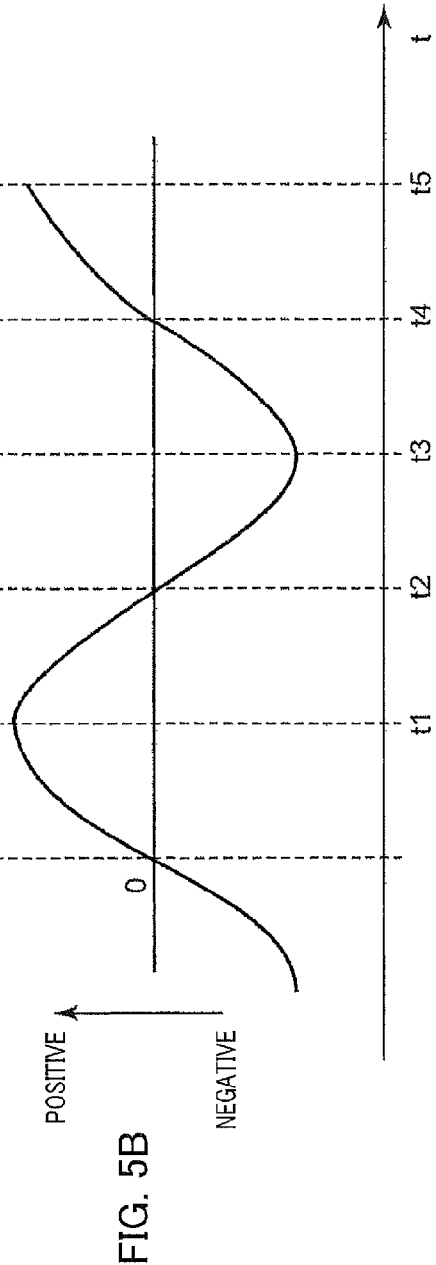
FIG. 5A
FIG. 5B

LINEAR ACTUATOR, ELECTRIC BRUSH, ELECTRIC CUTTING MACHINE AND ELECTRIC AIR PUMP

CROSS REFERENCE TO RELATED APPLICATIONS

This application is entitled to and claims the benefit of Japanese Patent Application No. 2014-201783, filed on Sep. 30, 2014, the disclosure of which including the specification, drawings and abstract is incorporated herein by reference in its entirety.

TECHNICAL FIELD

The present invention relates to a linear actuator that provides linear power, an electric brush, an electric cutting machine and an electric air pump.

BACKGROUND ART

Conventionally, in electric brushes used in facial equipment, electric toothbrushes, electric razors, electric shoeshine machines, electric car-washing machines and the like, a movable part such as a brush head of facial equipment, a brush part of a toothbrush, a blade, a shoe polishing brush, and a car-washing brush reciprocates for aesthetic cares of skin, teeth, shaving and the like, and for polishing and washing of shoes and a car body. In addition, conventionally, in electric cutting machines such as electric saws and electric gravers, a movable part such as a blade of a saw and a blade of a graver reciprocates for processing such as cutting, shaving, and carving of wood, metal, and the like. Further, conventionally, in electric air pumps used in sphygmomanometers, a movable part of a diaphragm reciprocates for air intake and exhaust of the electric air pump.

As a structure for driving the movable part of electric brushes, electric cutting machines, and electric air pumps, a structure that converts the normal axial rotation of DC motor into linear reciprocation or rotational reciprocation with use of a motion direction conversion mechanism is often used. Such a structure in which a motion direction conversion mechanism is used requires the space for the complicated mechanism for converting the driving direction, and therefore cannot be easily downsized. In addition, the motion conversion mechanism generates significant noise at the time of driving, and causes power loss, and therefore the efficiency may be sacrificed. Under such circumstances, structures of actuators have been proposed in which a movable part is linearly reciprocated (see, for example, PTLS 1 to 3).

In PTL 1, a vibration-type linear actuator used in a reciprocation-type electric shaver and the like is disclosed. In this linear actuator, a movable member having a magnet disposed with its magnetization direction set to a lateral direction is disposed on an electromagnet of a stator, and the movable member (magnet) is reciprocated in the lateral direction with respect to the stator.

In addition, PTL 2 discloses a cylindrical linear drive actuator which can be mounted in cylindrical equipment such as a toothbrush. In this actuator, a plunger is provided on the outer periphery of a shaft serving as a moving object, and two ring-shaped magnets sandwiching a coil are inserted on the outer periphery of the plunger together with the coil. The coil is electrified to excite the plunger such that the plunger functions as an electromagnet, and thus the shaft is moved in the axis direction.

In addition, PTL 3 discloses a vibrator as a structure for linear reciprocation of a movable member. In this vibrator, a coil supported by a substrate is disposed to face a vibrating member which can vibrate in the axis direction of the coil. In the vibrating member, a magnet is disposed at the center of an annular spindle, and the magnet is supported by the spindle through a leaf spring disposed to surround the magnet such that the magnet can be moved in the axis direction of the coil.

CITATION LIST

Patent Literature

PTL 1
 Japanese Patent Application Laid-Open No. 2005-160134
PTL 2
 Japanese Patent Publication No. 3475949
PTL 3
 Japanese Patent Application Laid-Open No. 2013-233537

SUMMARY OF INVENTION

Technical Problem

In PTL 1, however, the movable member (magnet) serving as the movable part is reciprocated with respect to the stator in the lateral direction. With this structure, when the structure is mounted in cylindrical equipment such as an electric toothbrush, a space for disposing the stator and the movable member side by side and a lateral space orthogonal to the space are required to be ensured so that the movable member is movable, thus making it difficult to achieve downsizing of the product. In addition, in PTL 2, the structure can be mounted in cylindrical equipment; however, a large number of components are required since a plurality of magnets are used, and therefore assemblability may be sacrificed and cost may be high. In PTL 3, a shaft for supporting a moving member (movable part) is not provided and the vibrator itself vibrates, and therefore it is difficult to achieve linear driving with an attachment such as a razor blade and a toothbrush which is required when it is applied to cylindrical electric aesthetic equipment.

An object of the present invention is to provide a linear actuator, an electric brush, an electric cutting machine, and an electric air pump which can achieve downsizing with a simple configuration, and can provide stable linear reciprocation while achieving improvement in assemblability and cost reduction.

Solution to Problem

To achieve the above-mentioned object, a linear actuator includes: an electromagnet including a coil; a magnet disposed to face the coil in a coil-winding axis direction of the coil and magnetized in a unipolar fashion in the coil-winding axis direction; a movable member including one of the electromagnet and the magnet and including an output shaft extending in the coil-winding axis direction; a fixing body including the other of the electromagnet and the magnet; an elastic body disposed along the coil-winding axis direction and configured to elastically deform in the coil-winding axis direction to support the movable member such that the movable member is allowed to reciprocate in the coil-winding axis direction; and an alternating-current supplying section configured to supply an alternating current having a frequency substantially equal to a resonance frequency of the movable member to the coil, in which a first end portion of the elastic body is fixed to the fixing body and a second end portion of the elastic body is fixed to the movable member in the coil-winding axis direction such that an air gap is formed between the electromagnet and the magnet.

An electric brush, an electric cutting machine, and an electric air pump of the embodiments of the present invention each include the actuator having the above-mentioned configuration.

Advantageous Effects of Invention

According to the present invention, an electromagnet coil and a magnet whose magnetization direction is set to the coil-winding axis are disposed to face each other in the coil-winding axis direction, and a movable member is supported in a fixing body by an elastic body fixed at its both end portions in the coil-winding axis direction such that the movable member can reciprocate in the coil-winding axis direction. With this configuration, downsizing can be achieved with a simple configuration, and stable linear reciprocation can be provided while achieving improvement in assemblability and cost reduction.

BRIEF DESCRIPTION OF DRAWINGS

FIGS. 5A and 5B show a cycle of an alternating current supplied to a coil from an alternating-current supplying section in the actuator according to Embodiment 1 of the present invention;

DESCRIPTION OF EMBODIMENTS

In the following, embodiments of the present invention will be described in detail with reference to the accompanying drawings.

Embodiment 1

Figure 1:
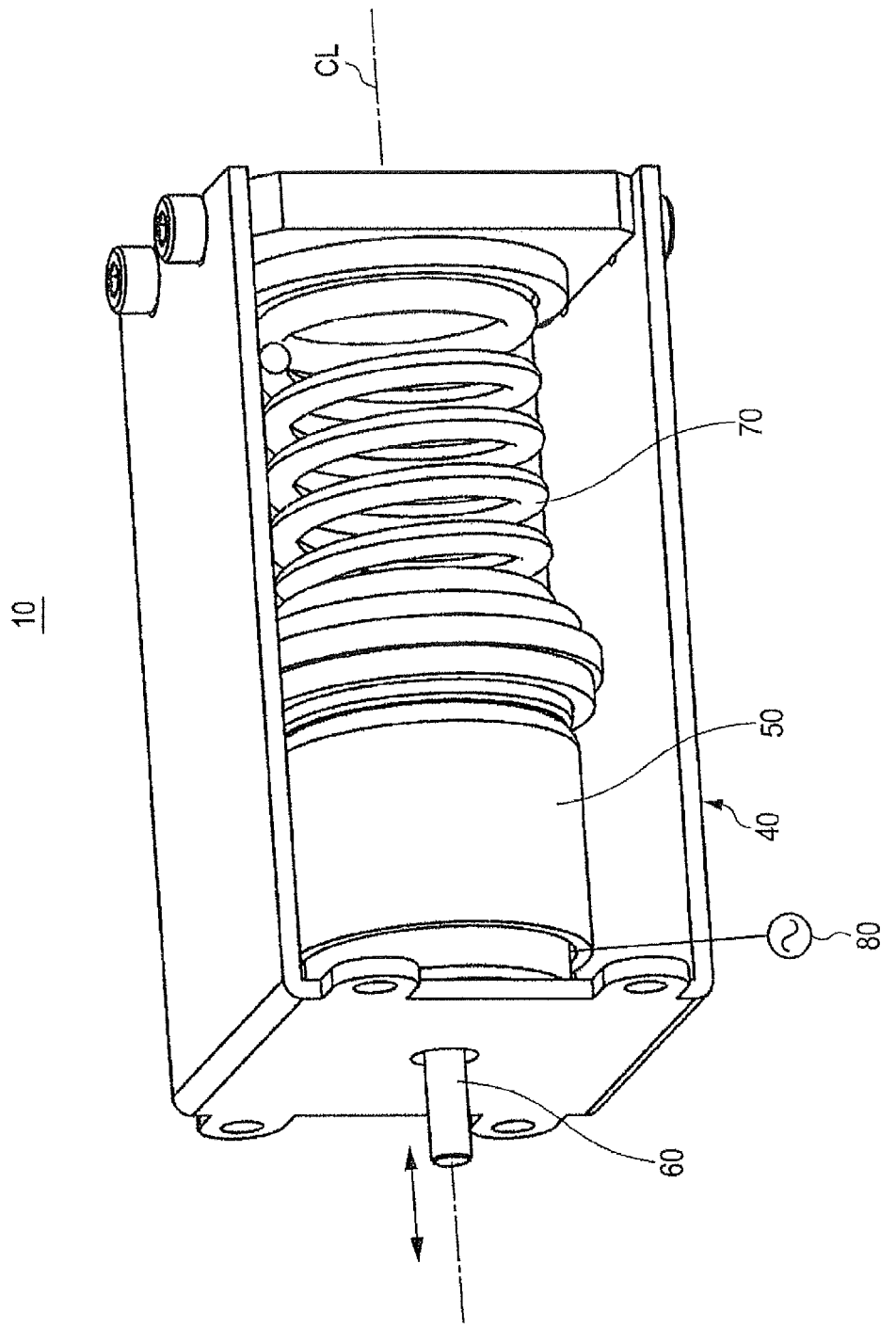
FIG. 1 illustrates an external appearance of a linear actuator according to Embodiment 1 of the present invention.
Figure 2:
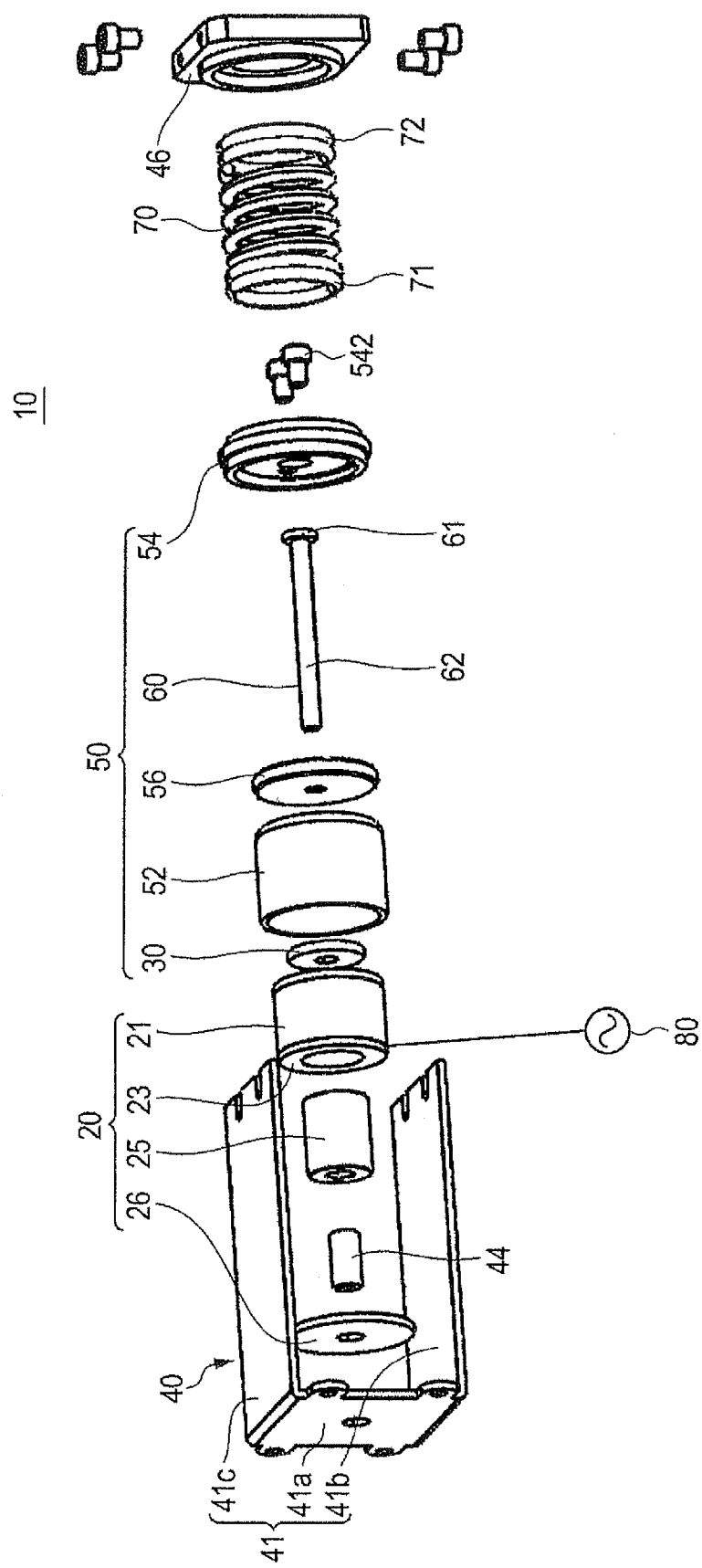
FIG. 2 is an exploded perspective view of the linear actuator according to Embodiment 1 of the present invention.

FIG. 1 illustrates an external appearance of a linear actuator according to Embodiment 1 of the present invention, and FIG. 2 is an exploded perspective view of the linear actuator.

Linear actuator 10 illustrated in FIG. 1 and FIG. 2 includes fixing body 40, movable member 50 including output shaft 60, and elastic body 70 that supports movable member 50 in fixing body 40 such that movable member 50 is movable along an axis (CL) direction of output shaft 60.

In linear actuator 10 illustrated in FIG. 1 and FIG. 2, movable member 50 reciprocates along the axis CL direction with respect to fixing body 40 with power supplied from alternating-current supplying section 80, and output shaft 60 reciprocates along the axis CL direction (indicated by arrow in FIG. 1) along with the reciprocation of movable member 50, whereby the reciprocation is output to the outside.

Figure 3:
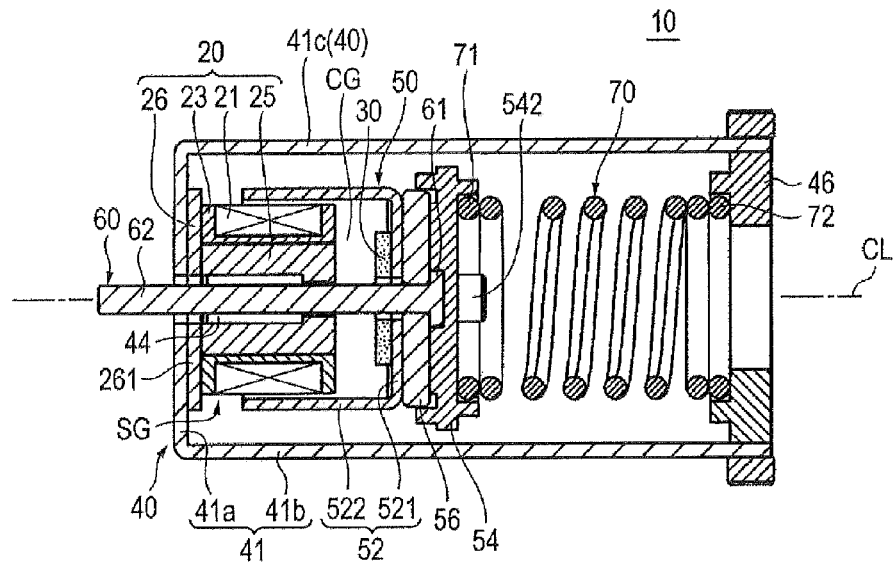
FIG. 3 is a schematic sectional view illustrating a configuration of a main part of the linear actuator according to Embodiment 1 of the present invention.

FIG. 3 is a schematic sectional view illustrating a configuration of a main part of the linear actuator.

As illustrated in FIG. 2 and FIG. 3, linear actuator 10 includes electromagnet 20 having coil 21, and magnet 30. Magnet 30 is disposed to face coil 21 in a coil-winding axis (which corresponds to axis CL of output shaft 60) direction of coil 21, and is magnetized in a unipolar fashion in the coil-winding axis direction of coil 21.

As illustrated in FIG. 2 and FIG. 3, in linear actuator 10, electromagnet 20 is provided on fixing body 40 side, and magnet 30 is provided on movable member 50 side.

Fixing body 40 includes electromagnet 20, baseplate 41, bearing 44, and spring receiving part 46.

Electromagnet 20 includes coil 21, bobbin 23, and main body core 25, and main body core 25 is integrally joined with plate core 26.

Bobbin 23 is formed of a non-magnetic substance, and has flanges at both end portions of its cylindrical body. Coil 21 is wound on the outer periphery of the body of bobbin 23 with the central axis of bobbin 23 as its winding axis (which corresponds to axis CL, and therefore is hereinafter referred to also as coil-winding axis CL). Bobbin 23 on which coil 21 is wound has a cylindrical shape in its entirety.

The coil winding of coil 21 is connected with a substrate not illustrated, and is connected to an external terminal through the substrate. Alternating current power (alternating current voltage) is supplied to coil 21 from alternating-current supplying section 80 through the external terminal.

Main body core 25 is formed of a magnetic substance, and is fitted with the internal side of the body of bobbin 23 in such a manner as to extend in the axial direction. Main body core 25 has a cylindrical shape, and in this case, and has a length equal to the axial length of bobbin 23. Bearing 44 through which output shaft 60 is movably inserted is attached inside main body core 25.

Together with main body core 25, bobbin 23 on which coil 21 is wound is closely fitted with plate core 26. Plate core 26 is formed of a magnetic substance, and functions as a core having a T-shaped cross section which is integrated with main body core 25 on the fixing side. Together with plate core 26, coil 21, bobbin 23 and main body core 25 are fixed to baseplate 41.

Baseplate 41 includes front plate part 41a which is orthogonal to coil-winding axis CL and through which output shaft 60 is loosely inserted, and side plate parts 41b and 41c which extend along coil-winding axis CL from respective ends, which are parallel to each other, of front plate part 41a to cover electromagnet 20 and magnet 30.

Baseplate 41 is formed of a non-magnetic substance such as aluminum, and has a U-shape in cross section with front plate part 41a and side plate parts 41b and 41c. In baseplate 41, coil 21, bobbin 23 and main body core 25 are fixed on the rear surface (rear side surface) side of front plate part 41a through plate core 26, and coil 21, bobbin 23 and main body core 25 are covered with side plate parts 41b and 41c in such a manner as to sandwich coil 21, bobbin 23 and main body core 25.

Across the ends (rear ends) of side plate parts 41b and 41c that are opposite to the ends at which front plate part 41a and side plate parts 41b and 41c are joined together, spring receiving part 46 that receives elastic body (coil spring) 70 that supports movable member 50 disposed in baseplate 41 is disposed.

Spring receiving part 46 is disposed parallel to front plate part 41a, and is firmly fixed to the ends (rear ends) of side plate parts 41b and 41c with a bolt. With this configuration, baseplate 41 and spring receiving part 46 form an actuator frame having a rectangular frame shape that houses a magnetic circuit having electromagnet 20 and magnet 30.

Movable member 50 includes magnet 30, output shaft 60, yoke 52, movable side receiving part 54 that receives the elastic body (spring) on the movable side, and bonding plate 56.

Magnet 30 has an annular shape having its thickness along the coil-winding axis CL direction, and is magnetized along the thickness direction. That is, magnet 30 is disposed such that its magnetization direction is set to the coil-winding axis CL direction. Magnet 30 is separated from electromagnet 20 (to be more specific, main body core 25) by a predetermined gap (central air gap CG). In this case, magnet 30 is fixed on yoke bottom surface 521 of cup-shaped yoke 52 that opens to electromagnet 20 side. Magnet 30 may be composed of, for example, a neodymium magnet (such as a neodymium sintered magnet and a neodymium bonding magnet). With use of a neodymium magnet, energy conversion efficiency can be enhanced even when the size is small, and actuator 10 can be downsized.

Yoke 52 is formed of a magnetic substance, and is formed in a cup shape by drawing. To be more specific, yoke peripheral wall 522 that protrudes toward electromagnet 20 side from the outer periphery of yoke bottom surface 521 on which magnet 30 is fixed is formed. Yoke peripheral wall 522 is provided over the outer periphery of coil 21 of electromagnet 20 so as to be movable along the coil-winding axis CL direction. The opening end of yoke peripheral wall 522 faces the external edge 261 of plate core 26 with a predetermined gap (outer air gap SG) therebetween on the outer periphery side of coil 21.

Together with magnet 30 and electromagnet 20 (mainly, coil 21 wound around bobbin 23, main body core 25, plate core 26 and the like), yoke 52 serves as a magnetic circuit.

Bonding plate 56 having an outer diameter substantially equal to that of yoke bottom surface 521 is fixed on the rear end surface of yoke bottom surface 521 of yoke 52, and movable side receiving part 54 is fixed to yoke 52 through bonding plate 56. In this case, movable side receiving part 54 is firmly fixed on bonding plate 56 with securing member 542 such as a screw.

In actuator 10, magnet 30, yoke bottom surface 521, bonding plate 56 and movable side receiving part 54 are attached along coil-winding axis (the axis of output shaft 60) CL with coil-winding axis CL as the center. In addition, output shaft 60 extending along coil-winding axis CL is disposed at center portions of magnet 30, yoke bottom surface 521 and bonding plate 56.

Flange 61 provided at one end (rear end) of output shaft 60 is sandwiched between bonding plate 56 and movable side receiving part 54 in the coil-winding axis CL direction such that output shaft 60 is integrally provided to movable member 50, and thus output shaft 60 is disposed along coil-winding axis CL. Shaft 62 extending from flange 61 is inserted to bearing 44 on fixing body 40 side in yoke 52 through bonding plate 56, yoke bottom surface 521 and magnet 30. With this configuration, the free end of shaft 62, that is, the other end of output shaft 60 protrudes from front plate part 41a of baseplate 41.

Elastic body 70 is interposed between movable side receiving part 54 and spring receiving part 46 on fixing body 40 side along the coil-winding axis CL direction.

Elastic body 70 elastically deforms in the coil-winding axis CL direction, and the both ends in the coil-winding axis CL direction move in a direction along which the both ends are brought closer to or separated from each other (contacting or separating direction). With this configuration, movable side receiving part 54 and spring receiving part 46 on fixing body 40 side can move in the contacting or separating direction along coil-winding axis CL with deformation of elastic body 70.

The central axis of elastic body 70, the coil-winding axis of coil 21, the axis of output shaft 60, and the central axis of magnet 30 are aligned or substantially aligned as axis CL. In this case, elastic body 70, coil 21, bobbin 23, output shaft 60, magnet 30 and the like are disposed such that the axes are aligned along the same axis.

In this case, elastic body 70 is composed of a coil spring, and its central axis as its coil-winding axis is set to coil-winding axis CL.

Both ends 71 and 72 of elastic body 70 on both sides in the coil-winding axis CL direction are fixed to movable side receiving part 54 and spring receiving part 46, respectively. With this configuration, elastic body 70 supports movable member 50 from the rear end side of fixing body 40 in a cantilever state in the coil-winding axis CL direction.

In addition, in a normal state (non-driving state), elastic body 70 supports movable member 50 with respect to fixing body 40 such that central air gap CG and outer air gap SG are formed. Air gaps CG and SG allow movable member 50 to reciprocate along the coil-winding axis CL direction. In this manner, in linear actuator 10, elastic body 70 provides given air gaps CG and SG between movable member 50 and fixing body 40 even when an attraction force is generated by magnet 30 between linear actuator 10 and main body core 25 in a non-driving state.

Elastic body (coil spring) 70 can obtain a given spring constant $K_{s\,p}$ [N/m] with respect to the movement direction of magnet 30, and movable member 50 reciprocates in the actuator frame of fixing body 40 in the coil-winding axis CL direction of output shaft 60 when alternating current power is supplied to magnetic circuit coil 21. Elastic body 70 can adjust the resonance frequency in linear actuator 10.

In linear actuator 10 of the present embodiment, movable member 50 vibrates relative to fixing body 40 with resonance frequency $f_0$ [Hz] which is calculated by the following Expression 1.

[Expression 1]

$$f_0 = \frac{1}{2\pi}\sqrt{\frac{K_{sp}}{m}} \quad \text{Expression 1}$$

Where the mass of movable member 50 is represented by m [Kg], the spring constant of elastic body 70 in the coil-winding axis direction is represented by $K_{s\,p}$, and $f_0$ represents resonance frequency [Hz].

In linear actuator 10 of Embodiment 1, alternating-current supplying section 80 supplies coil 21 with an alternating current having a frequency substantially equal to resonance frequency $f_0$ [Hz] of movable member 50. With this configuration, movable member 50 can be driven in a resonance state and can be driven with low power consumption in a normal state, and thus, energy efficiency can be enhanced while ensuring a large output.

Movable member 50 in linear actuator 10 is supported with a spring-mass structure by fixing body 40 through elastic body 70. Thus, when coil 21 is supplied with an alternating current having a frequency equal to resonance frequency $f_0$ [Hz] of movable member 50, movable member 50 is driven in a resonance state. The reciprocation generated at this time in the axial direction is transmitted to output shaft 60 of movable member 50.

Linear actuator 10 is driven based on the equation of motion of the following Expression 2 and the circuit equation of the following Expression 3.

[Expression 2]

$$m\frac{d^2x(t)}{dt^2} = K_f i(t) - K_{sp}x(t) - D\frac{dx(t)}{dt} \quad \text{Expression 2}$$

m: Mass [Kg]
x (t): Displacement [m]

t: Time [sec]
Kf: Thrust constant [N/A]
i (t): Current [A]
Ksp: Spring constant [N/m]
D: Attenuation coefficient [N/(m/s)]

[Expression 3]

$$e(t) = Ri(t) + L\frac{di(t)}{dt} + K_t\frac{dx(t)}{dt} \quad \text{Expression 3}$$

e (t): Voltage [V]
R: Resistance [Ω]
L: Inductance [H]
Kt: Counter electromotive force constant [V/(m/s)]

It is to be noted that mass m [Kg] of movable member 50, displacement x (t)[m], thrust constant Kf [N/A], current i (t)[A], spring constant $K_{s\,p}$ [N/m], attenuation coefficient D [N/(m/s)] and the like in linear actuator 10 may be appropriately changed as long as Expression 2 is satisfied. Likewise, voltage e (t)[V], resistance R [Ω], inductance L [H], and counter electromotive force constant $K_t$ [V/(m/s)] may be appropriately changed as long as Expression 3 is satisfied.

In linear actuator 10, in a non-driving state (when coil 21 is not electrified), a magnetic circuit is formed in which the magnetic flux generated from magnet 30 goes through central air gap CG, main body core 25, outer air gap SG and yoke 52, and is connected with the counter electrode of magnet 30. When a current is applied to coil 21, coil 21 and main body core 25 act as an electromagnet, thus generating an attraction or repulsive force with respect to magnet 30 which face coil 21 and main body core 25 in the axial direction. At this time, since movable member 50 is supported by elastic body 70 in the axis (coil-winding axis CL) direction of output shaft 60 and output shaft 60 is supported by bearing 44, movable member 50 linearly moves in the axial direction. Further, by applying an alternating current voltage to coil 21, linear reciprocation is achieved.

Next, an operation of linear actuator 10 is specifically described with a flow of magnetic flux in a magnetic circuit.

Figure 4:
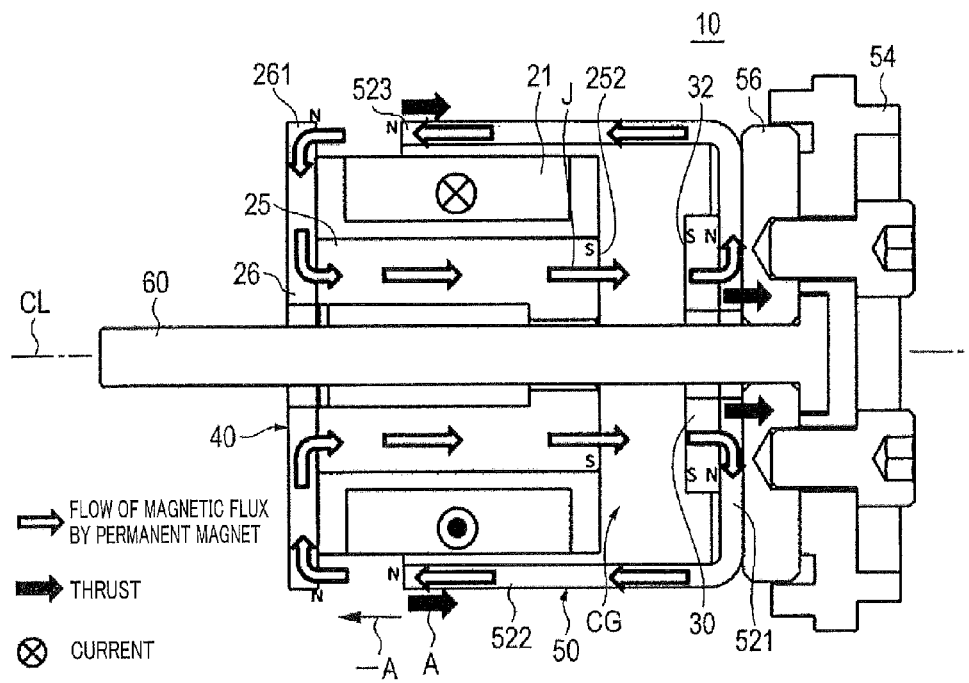
FIG. 4 is a planer sectional view illustrating a magnetic circuit of the linear actuator according to Embodiment 1 of the present invention.

FIG. 4 is a planer sectional view illustrating a magnetic circuit of linear actuator 10. In addition, FIGS. 5A and 5B show a cycle of an alternating current supplied from the alternating-current supplying section to coil 21 of fixing body 40 through a substrate not illustrated in linear actuator 10 of the present embodiment. It is to be noted that the alternating current flowing through coil 21 may be a pulse wave having a frequency of $f_0$ as illustrated in FIG. 5A, or may be a sine wave having a frequency of $f_0$ as illustrated in FIG. 5B.

In linear actuator 10 illustrated in FIG. 4, main body core 25 is excited by coil 21 when alternating current power is supplied to coil 21 (for example, supply of a current in the forward direction at time point t1 illustrated in FIGS. 5A and 5B). In this case, a flow of a magnetic flux is generated between end surface 252 of main body core 25 and opposing surface 32 of magnet 30 (center side gap CG) from main body core 25 to magnet 30. For example, when the flow of the magnetic flux generated at this time is indicated by arrow J, and magnetic flux J flows from main body core 25 to magnet 30, and from magnet 30 to yoke bottom surface 521 and yoke peripheral wall 522.

A current applied to coil 21 such that end surface 252 of main body core 25 has a polarity identical to the polarity (S pole) of opposing surface 32 of magnet 30 facing end surface 252. At this time, since the surface of magnet 30 has the polarity (S pole) same as that of the end surface of main body core 25, the S pole surface of magnet 30 facing thereto repulses. In addition, opening end 523 of yoke peripheral wall 522 of movable member 50 having magnet 30 has N polarity, and external edge 261 of plate core 26 facing thereto has N polarity. With this configuration, magnet 30 of movable member 50 and opening end 523 of yoke peripheral wall 522 repulse main body core 25 of fixing body 40 and external edge 261 of plate core 26, respectively, and move away from main body core 25 and the external edge of plate core 26 (in the thrust A direction). That is, with respect to end surface 252 of main body core 25 (fixing body 40), magnet 30 (movable member 50) moves to a position shifted from the position illustrated in FIG. 4 in the thrust A direction against the biasing force of elastic body 70.

Next, when the direction of the current is changed at time point t2 of FIG. 5, movable member 50 is moved to a reference position (the position illustrated in FIG. 4) by the restoration force of elastic body 70, and a current of the opposite direction is supplied from alternating-current supplying section (alternating current power source) 80 (see FIGS. 1 and 2) to coil 21 at time point t3 of FIG. 5. Then, in the state where movable member 50 is located at the reference position, end surface 252 of main body core 25 which faces magnet 30 has N polarity, and the end surface of main body core 25 on plate core 26 side has S polarity. As a result, the direction along which magnetic flux J flows is opposite to the direction shown in FIG. 4. That is, magnetic flux J sequentially flows from opposing surface of S pole of magnet 30 through main body core 25, plate core 26, external edge 261 of plate core 26, yoke peripheral wall 522, yoke bottom surface 521, and magnet 30. Consequently, end surface 252 acting as N pole of main body core 25 attracts opposing surface 32 acting as S pole of opposite magnet 30. At the same time, external edge 261 of plate core 26 acts as S pole, and therefore attracts opening end 523 of yoke peripheral wall 522 acting as N pole. With this configuration, magnet 30 of movable member 50 and opening end 523 of yoke peripheral wall 522 are respectively attracted by main body core 25 of fixing body 40 and external edge 261 of plate core 26, and are brought closer to main body core 25 and external edge 261 of plate core 26. To be more specific, magnet 30 and opening end 523 of yoke peripheral wall 522 located at the reference position shown in FIG. 4 move from the reference position in the thrust-A direction, and move to positions close to end surface 252 and external edge 261 of plate core 26.

Then the direction of the current is changed as shown in time point t4 of FIGS. 5A and 5B, and when movable member 50 is reset to the reference position, a current in the forward direction at time point t5 of FIGS. 5A and 5B is supplied. The operations described above are carried out in one cycle, and when the operations are repeated, magnet 30 of movable member 50 repeats movement in the −A direction and the thrust A direction, that is, the coil-winding axis CL direction, with the reference position of the state illustrated in FIG. 4 which is identical to the non-driving state, that is, the state where it is held by elastic body 70. Thus, through magnet 30, output shaft 60 reciprocates in the axial direction of output shaft 60, that is, coil-winding axis CL.

As described, according to the present embodiment, magnet 30 of movable member 50 is disposed to face coil 21 of the electromagnet of fixing body 40 in the coil-winding axis CL direction. Magnet 30 is magnetized in a unipolar fashion in the coil-winding axis CL direction, and movable member 50 further includes output shaft 60 extending in the coil-winding axis CL direction. In addition, movable member 50 is supported by elastic body 70 in fixing body 40 such that movable member 50 can reciprocate along the coil-winding axis CL direction. Elastic body 70 is disposed along the coil-winding axis CL direction, and is configured to deform in the coil-winding axis CL direction. Elastic body 70 is fixed to fixing body 40 and movable member 50 at both ends 71 and 72 in the coil-winding axis direction. When an alternating current having a frequency substantially equal to the resonance frequency of movable member 50 is supplied to coil 21 from alternating-current supplying section 80, movable member 50 is reciprocated with a high output by the above-described magnetic circuit in the axis (coil-winding axis CL) direction of output shaft 60.

As described, in linear actuator 10, fixing body 40, and magnet 30 of movable member 50 arranged in the coil-winding axis CL direction with respect to coil 21 of the electromagnet of fixing body 40 are respectively fixed by elastic body 70 at both ends 71 and 72 in the coil-winding axis CL direction. That is, in linear actuator 10, magnet 30, electromagnet (coil 21), and elastic body 70 are disposed along the coil-winding axis direction that is the reciprocation direction of output shaft 60. In linear actuator 10, magnet 30, electromagnet (coil 21) and elastic body 70 are disposed side by side in the coil-winding axis CL direction.

With this configuration, linear actuator 10 can be formed in a linear shape in its entirety, and thus, simple and small-sized linear actuator 10 with high output can be achieved. In addition, since single unipolar magnet 30 is used, the number of components can be reduced, and stable linear reciprocation can be provided while achieving improvement in assemblability and cost reduction.

In addition, output shaft 60 of movable member 50 is movably inserted through bearing 44 in main body core 25 formed of a magnetic substance disposed in bobbin 23 in electromagnet 20 of fixing body 40 in the coil-winding axis CL direction. With this configuration, output shaft 60 can be supported without being bent such that output shaft 60 can be linearly driven even in the case where unexpected external force such as impact of dropping is exerted.

In addition, elastic body 70 is composed of a coil spring, and therefore, even when large driving deformation is caused, the function of a linear spring can be ensured, and stable linear reciprocation with respect to movable member 50 can be achieved. In addition, since the stress of elastic body 70 is dispersed to the entire coil spring, reliability can be enhanced.

In addition, in the magnetic circuit, yoke 52 on movable member 50 side which has magnet 30 opens to electromagnet 20 side which has coil 21 in fixing body 40, and yoke 52 is disposed over coil 21. With this configuration, energy conversion efficiency can be enhanced without wasting the magnetic flux generated by magnet 30. In addition, since yoke peripheral wall 522 of yoke 52 is disposed to cover the outer periphery of electromagnet 20, the actuator can be downsized. In addition, since coil 21 is provided in fixing body 40, the drawing line of the element wire of the coil 21 can be easily pulled out, and enhancement of assemblability is achieved.

Embodiment 2

Figure 6:
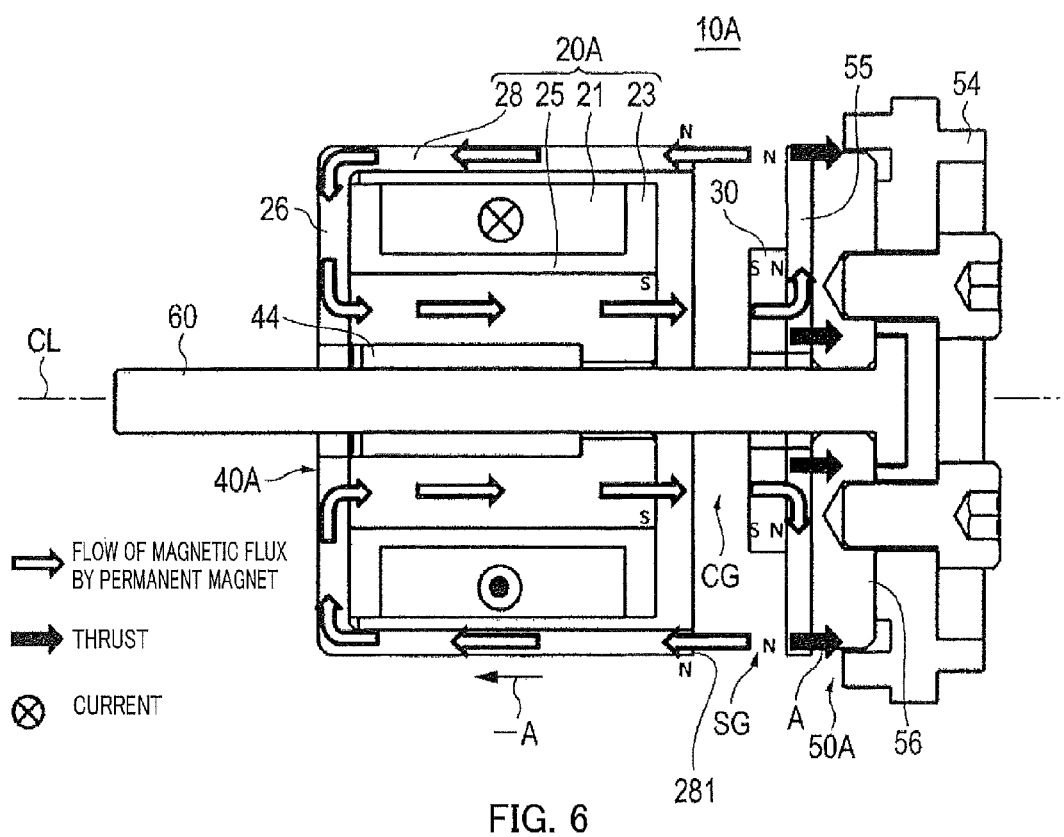
FIG. 6 illustrates a linear actuator according to Embodiment 2 of the present invention.

FIG. 6 is a planer sectional view illustrating a magnetic circuit of linear actuator 10A according to Embodiment 2 of the present invention.

Linear actuator 10A illustrated in FIG. 6 has a basic configuration similar to that of linear actuator 10 of Embodiment 1 illustrated in FIGS. 1 to 4. Linear actuator 10A differs from linear actuator 10 in the shape of the yoke (yoke 52 in linear actuator 10) on movable member 50 side that is a part of a magnetic circuit and in the shape of the core (plate core 26 in linear actuator 10) on fixing body 40 side. Since functions and shapes of other configurations are similar to those of linear actuator 10, the same components are denoted by the same reference numerals, and the description thereof will be omitted.

Linear actuator 10A illustrated in FIG. 6 includes fixing body 40A including electromagnet 20A and an actuator frame not illustrated (baseplate 41 and spring receiving part 46 illustrated in FIG. 2 and FIG. 3), and movable member 50A having output shaft 60. As in linear actuator 10, movable member 50A is supported by elastic body 70 (see FIGS. 1 to 3) in the actuator frame of fixing body 40A such that movable member 50A is movable in the axis (coil-winding axis CL) direction of output shaft 60.

Linear actuator 10A has a configuration in which, in the configuration of linear actuator 10, plate-shaped plate yoke 55 serving as a magnetic substance is applied in place of cup-shaped yoke 52, and cup-shaped magnetic case 28 serving as a magnetic substance in which plate core 26 serves as a bottom plate is applied for covering one surface of plate-shaped plate yoke 55 in place of plate core 26. With this configuration, the flow of the magnetic flux illustrated in FIG. 6 is achieved, and the magnetic circuit is similar to that of linear actuator 10 and operates in a manner similar to that of linear actuator 10, whereby output shaft 60 linearly reciprocates in the coil-winding axis CL direction (thrust A direction and −A direction).

Linear actuator 10A may have a configuration in which, in the configuration of linear actuator 10, magnetic case 28 serves as yoke 52 and plate yoke 55 serves as plate core 26 for example. With this configuration, movable member 50A reciprocates with respect to fixing body 40A in the coil-winding axis CL direction with power supplied from alternating-current supplying section 80, and output shaft 60 reciprocates in the coil-winding axis CL direction along with the reciprocation of movable member 50A, whereby the reciprocation is output to the outside.

Consequently, in comparison with linear actuator 10, since cup-shaped yoke 52 that is a part of movable member 50 in linear actuator 10 is replaced by plate-shaped plate yoke 55, the weight of movable member 50A supported by elastic body 70 can be reduced.

With this configuration, in linear actuator 10A, components disposed near movable member 50A can be more freely designed, and the resonance frequency can be increased. Further, the weight of movable member 50A can be reduced, and therefore the energy required for driving movable member 50A can be reduced. In addition, opening end 281 of the cylindrical part that opens to movable member 50A side in magnetic case 28 has a hard stop structure in which opening end 281 makes contact with the external edge of plate yoke 55 when movable member 50A linearly reciprocates in the coil-winding axis CL direction. With this configuration, magnet 30 fixed to plate yoke 55 does not make contact with electromagnet 20A. It is to be noted that the effects of components having functions similar to those of the components of Embodiment 1 are similar to those of Embodiment 1, and therefore description thereof will be omitted. It is to be noted that the hard stop structure may be applied also in linear actuators 10 and 10B to 10D in the other embodiments.

Embodiment 3

Figure 7:
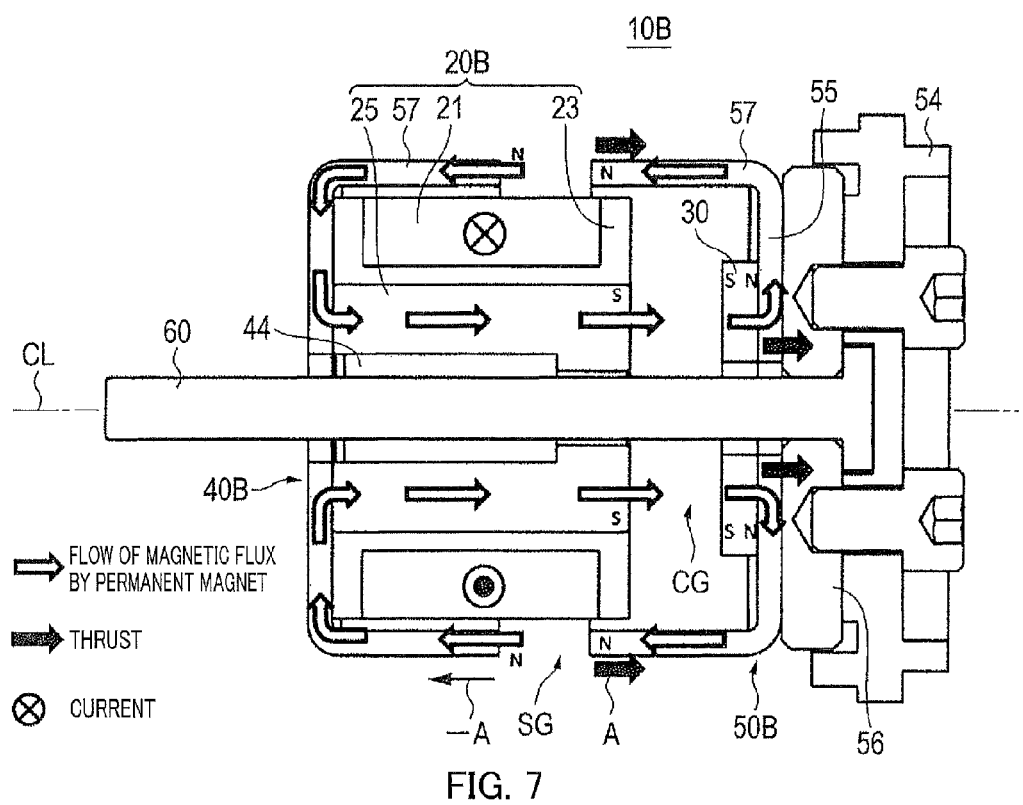
FIG. 7 illustrates a linear actuator according to Embodiment 3 of the present invention.

FIG. 7 is a planer sectional view illustrating a magnetic circuit of linear actuator 10B according to Embodiment 3 of the present invention.

Linear actuator 10B has a basic configuration similar to that of linear actuator 10 of Embodiment 1 illustrated in FIGS. 1 to 4. Linear actuator 10B differs from linear actuator 10 in the shape of the yoke on movable member 50 side that is a part of magnetic circuit (yoke 52 of actuator 10), and the shape of the core on fixing body 40 side (plate core 26 of actuator 10). Since functions and shapes of other configurations are similar to those of linear actuator 10, the same components are denoted by the same reference numerals, and the description thereof will be omitted.

Linear actuator 10B illustrated in FIG. 6 includes fixing body 40B including electromagnet 20B and an actuator frame not illustrated (baseplate 41 and spring receiving part 46 illustrated in FIG. 2 and FIG. 3), and movable member 50B having output shaft 60. Movable member 50B is supported by elastic body 70 (see FIGS. 1 to 3) in fixing body 40B such that movable member 50B is movable in the axis (coil-winding axis CL) direction of output shaft 60.

In linear actuator 10B, cup-shaped (bottomed cylindrical) yoke 52 and plate core 26 in linear actuator 10 are replaced by cup-shaped magnetic substance (which correspond to the bottomed cylindrical core and the yoke) 57 having a similar configuration.

That is, electromagnet 20B in linear actuator 10B is housed in cup-shaped magnetic substance 57 such that main body core 25 protruding from the center portion of the bottom plate of cup-shaped magnetic substance 57 is inserted to bobbin 23 on which coil 21 is wound. The bottom plate of cup-shaped magnetic substance 57 is provided with a hole which is in communication with bearing 44 fitted in main body core 25, and to which output shaft 60 is inserted. It is to be noted that, together with main body core 25, cup-shaped magnetic substance 57 functions as a core having an E-shape in cross-section in which coil 21 is disposed. As the magnetic circuit of linear actuator 10B, the flow of the magnetic flux illustrated in FIG. 7 is achieved, and the magnetic circuit is similar to that of linear actuator 10 and operates in a manner similar to that of linear actuator 10 and thus output shaft 60 linearly reciprocates in the coil-winding axis CL direction (thrust A direction and −A direction).

With this configuration, in linear actuator 10B, components (cup-shaped magnetic substance 57) having the same shape are used for the yoke fixed to magnet 30 on movable member 50B side, and the core portion that serves as electromagnet 20B on fixing body 40B side. With this configuration, since different members are not used for the yoke and the core portion, cost can be reduced. It is to be noted that the effects of the components having functions similar to those of the components of Embodiment 1 are similar to those of Embodiment 1, and therefore description thereof will be omitted.

Embodiment 4

Figure 8:
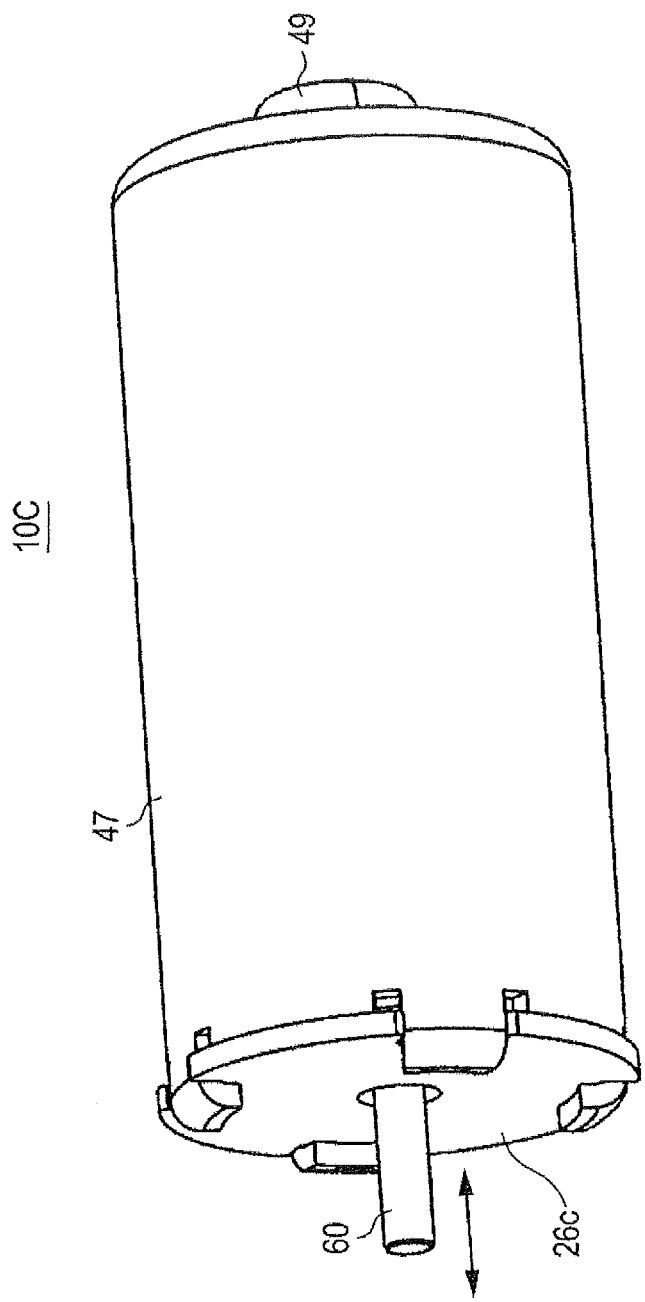
FIG. 8 is an external appearance view illustrating a linear actuator according to Embodiment 4 of the present invention.
Figure 9:
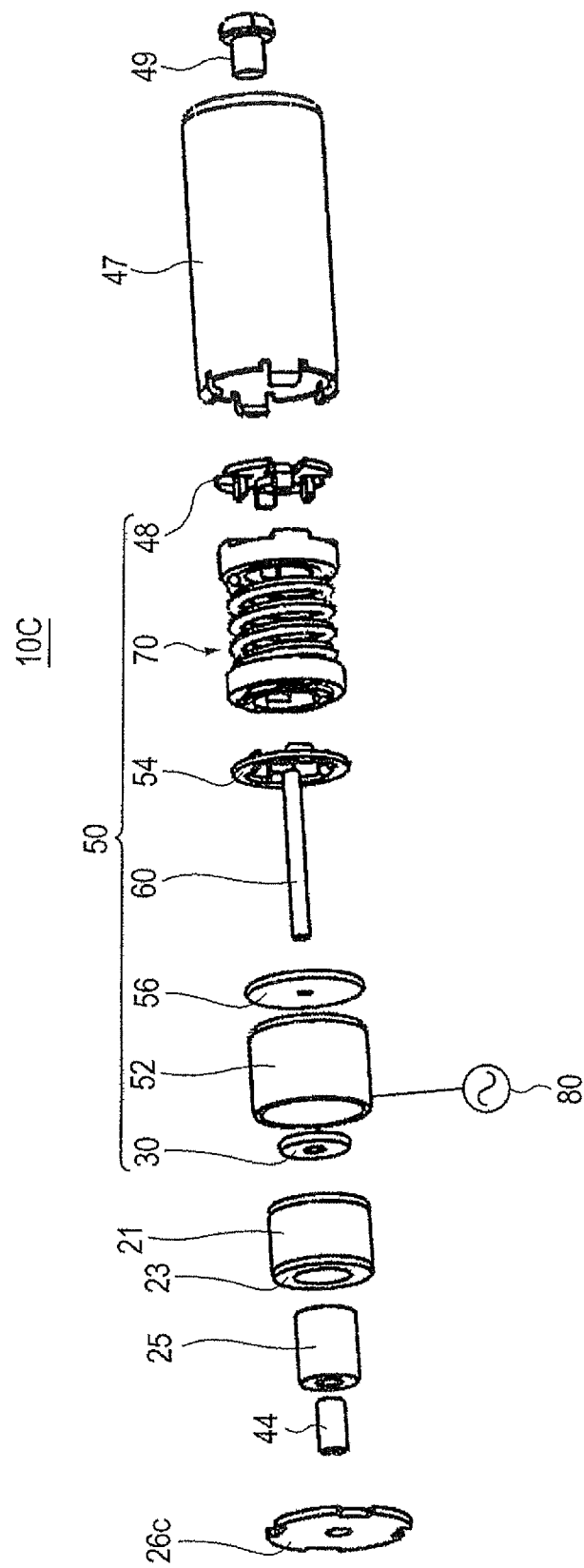
FIG. 9 is an exploded perspective view of the linear actuator according to Embodiment 4 of the present invention.
Figure 10:
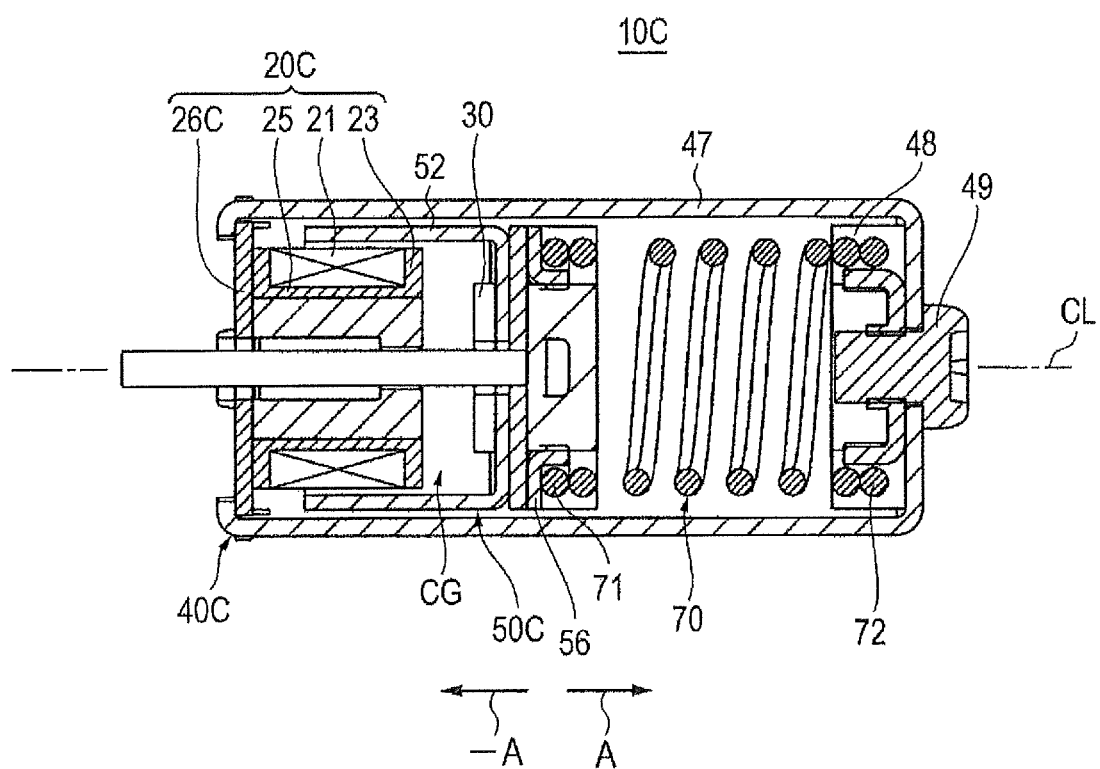
FIG. 10 is a schematic sectional view illustrating a configuration of a main part of the linear actuator according to Embodiment 4 of the present invention.

FIG. 8 illustrates an external appearance of linear actuator 10C according to Embodiment 4 of the present invention, and FIG. 9 is an exploded perspective view of linear actuator 10C. FIG. 10 is a schematic sectional view illustrating a configuration of a main part of linear actuator 10C.

It is to be noted that linear actuator 10C has a basic configuration similar to that of linear actuator 10 of Embodiment 1 illustrated in FIGS. 1 to 4, and therefore the same components are denoted by the same reference numerals, and the description thereof will be omitted.

Linear actuator 10C illustrated in FIG. 8 to FIG. 10 is an actuator having a configuration in which a part corresponding to baseplate 41 of fixing body 40 covers the entire linear actuator 10 in the configuration of linear actuator 10.

In the configuration of linear actuator 10, linear actuator 10C has cylindrical case 47 in place of baseplate 41 and case 47 covers a magnetic circuit similar to that of linear actuator 10.

That is, linear actuator 10C includes electromagnet 20 having coil 21, and magnet 30 disposed to face coil 21 in the coil-winding axis CL (which corresponds to output shaft 60 axis) direction of coil 21 and magnetized in a unipolar fashion in the coil-winding axis CL direction. Magnet 30 is provided in movable member 50C having a configuration similar to that of movable member 50, and supported through elastic body (coil spring) 70 in fixing body 40C so as to face coil 21 of electromagnet 20C with center side gap CG therebetween.

A core formed of a magnetic substance and composed of disk-shaped disk core 26C and main body core 25 fixed to disk core 26C is provided, and bobbin 23 is disposed over the outer surface of main body core 25, and coil 21 is wound around outer surface of bobbin 23. Thus, electromagnet 20C is obtained.

Fixing body 40C is configured by attaching disk core 26C of electromagnet 20C to the opening end of case 47 that opens on the front surface side so as to seal case 47.

Case 47 is formed of a non-magnetic substance such as aluminum and formed in a bottomed cylindrical shape, and movable member 50C and elastic body 70 are disposed in case 47. An opening is formed at the center of a bottom plate (which corresponds to the rear end) of case 47, and spring receiving part 48 that receives the other end 72 of elastic body 70 is fixed to the opening of the bottom plate with screw 49 from the outside. Movable member 50 is fixed at one end 71 of elastic body 70 in the coil-winding axis CL direction.

Spring receiving part 48 has a function similar to that of the spring receiving part of actuator 10, and receives and fixes an end portion of a coil spring serving as elastic body 70.

With this configuration, in case 47, movable member 50C is supported through elastic body 70 such that movable member 50C can reciprocate in the coil-winding axis direction (arrow A direction and −A direction) in the state where the outer surface of coil 21 of electromagnet 20C of fixing body 40C is surrounded by the peripheral wall of yoke 52. In addition to the operation and effect similar to those of linear actuator 10, the interior of linear actuator 10C including the magnetic circuit is covered with cylindrical case 47 in linear actuator 10C, and therefore foreign matters such as dust do not easily enter the interior, and thus reliability can be improved. In addition, when case 47 is made of a metal, it can serve as a countermeasure against noise. Further, when case 47 is made of a magnetic substance, leakage of the magnetic flux can be reduced.

Embodiment 5

Figure 11:
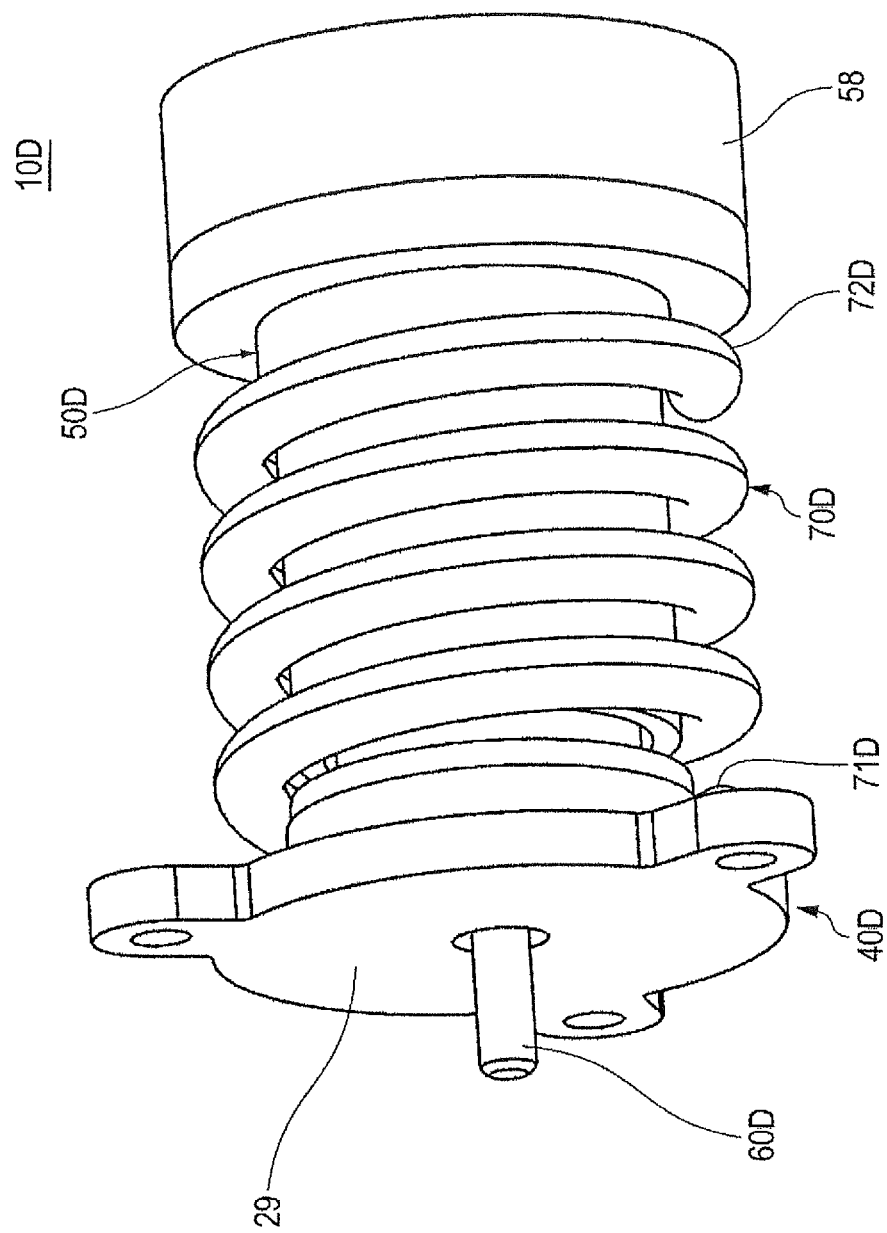
FIG. 11 is an external appearance view illustrating a linear actuator according to Embodiment 5 of the present invention.
Figure 12:
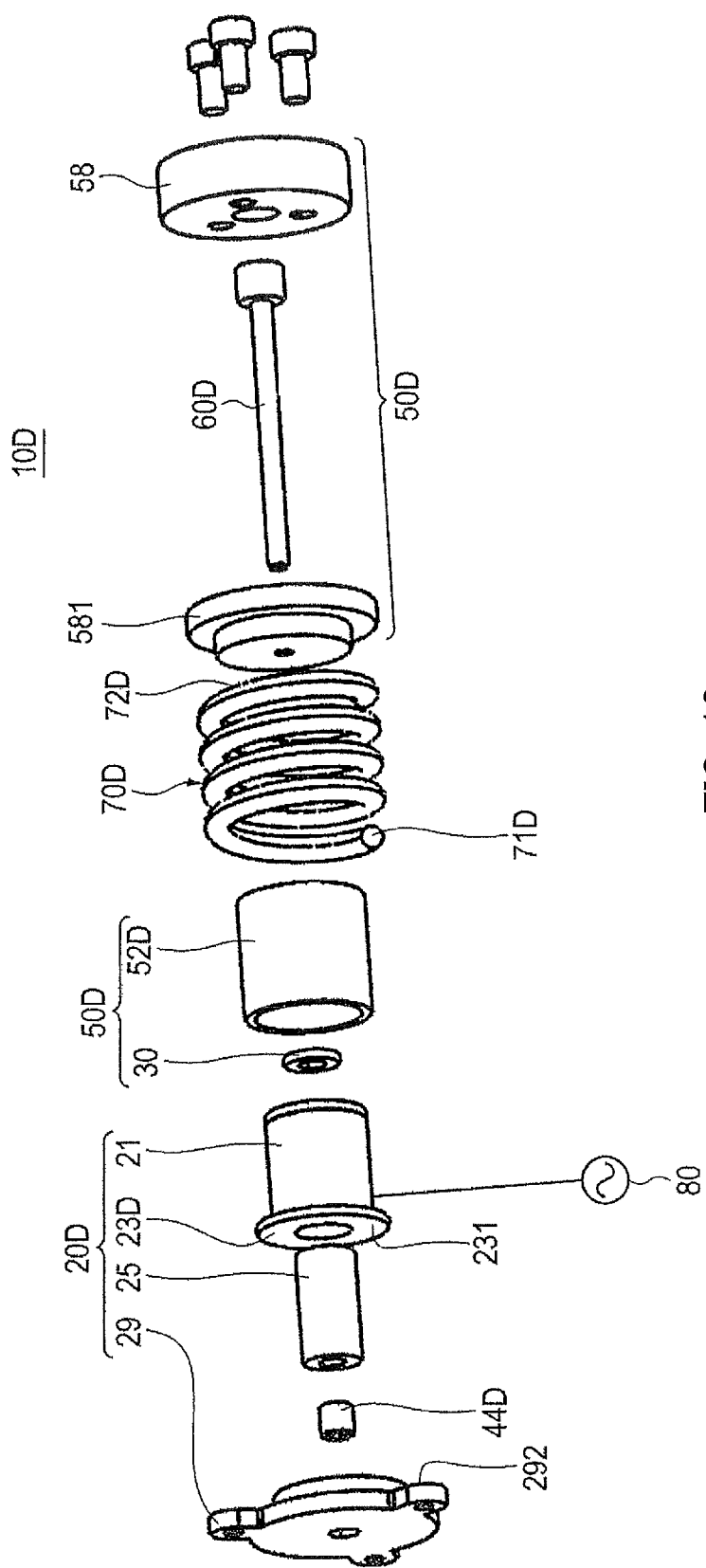
FIG. 12 is an exploded perspective view of the linear actuator according to Embodiment 5 of the present invention.
Figure 13:
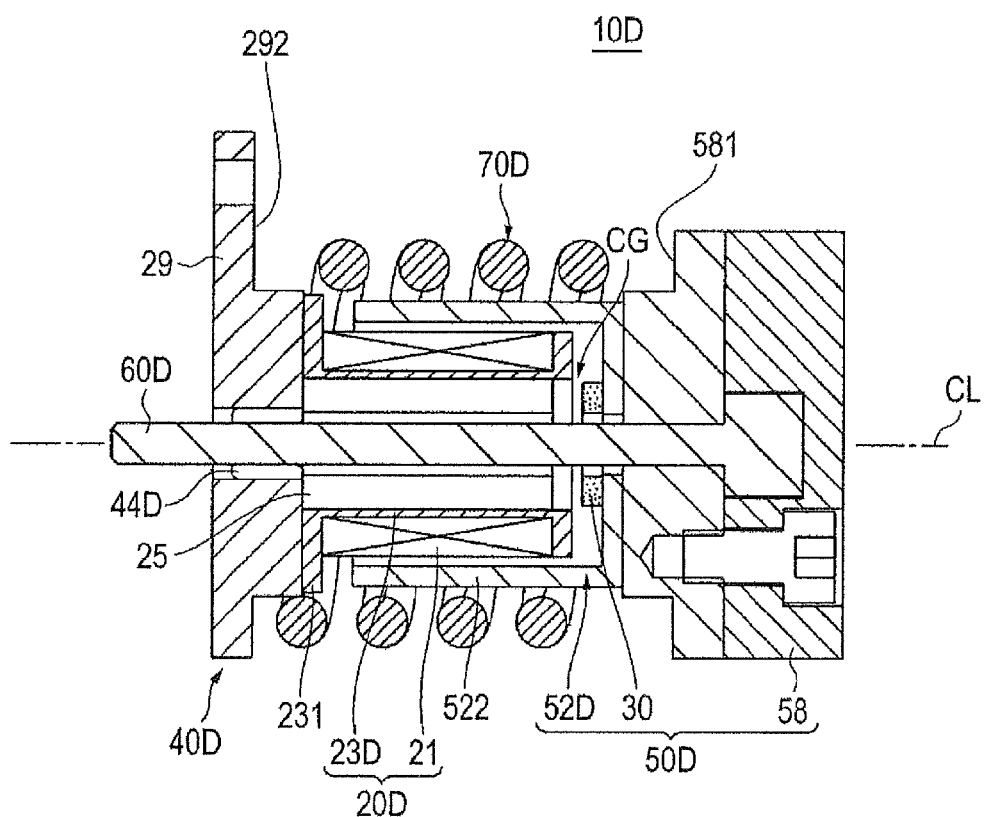
FIG. 13 is a schematic sectional view illustrating a configuration of a main part of the linear actuator according to Embodiment 5 of the present invention.

FIG. 11 is an external appearance view illustrating linear actuator 10D according to Embodiment 5 of the present invention, FIG. 12 is an exploded perspective view of linear actuator 10D, and FIG. 13 is a schematic sectional view of a configuration of a main part of linear actuator 10D.

It is to be noted that linear actuator 10D has a basic configuration similar to that of linear actuator 10 of Embodiment 1 illustrated in FIGS. 1 to 4 in terms of the magnetic circuit in particular. Therefore, the same components are denoted by the same reference numerals, and the description thereof will be omitted.

Linear actuator 10D illustrated in FIG. 11 and FIG. 12 includes electromagnet 20D having coil 21 and magnet 30 disposed to face coil 21 the coil-winding axis CL direction of coil 21 and magnetized in a unipolar fashion in the coil-winding axis direction.

In this case, magnet 30 is firmly fixed on the bottom surface inside cup-shaped yoke 52D, and is provided in movable member 50D with yoke 52D, output shaft 60D, and axis fixing part 58 that fixes output shaft 60D. Electromagnet 20D having coil 21 is provided to fixing body 40D. Magnet 30 of movable member 50D is supported through elastic body (coil spring) 70 in fixing body 40D such that magnet 30 face coil 21 of electromagnet 20C of fixing body 40 with center side gap CG therebetween and can reciprocate along the coil-winding axis CL direction of coil 21.

Fixing body 40D includes electromagnet 20D, bearing 44D, and front core part 29 fixed to one end of electromagnet 20D in coil-winding axis CL and through which output shaft 60D is movably inserted via bearing 44D.

As with Embodiment 1, electromagnet 20D includes coil 21 to which an alternating current is supplied from alternating-current supplying section 80 (see FIG. 12) and bobbin 23D on which coil 21 is wound. Bobbin 23D includes flange 231 and a cylindrical main body. Flange 231 is provided at one opening end of the cylindrical main body of bobbin 23D on which coil 21 is wound. Bobbin 23D is fixed to front core part 29 with flange 231.

Front core part 29 is formed of a magnetic substance, and formed in a plate shape. A magnetic circuit is composed of front core part 29, coil 21, yoke 52D, and magnet 30.

Front core part 29 is disposed such that it is orthogonal to the axis (which corresponds to coil-winding axis CL) of output shaft 60D. Output shaft 60D is inserted through the center portion of front core part 29 such that an end of output shaft 60D protrudes outside. Output shaft 60D is protruded from axis fixing part 58 of movable member 50D into yoke 52D, and is inserted to bearing 44D in bobbin 23D and magnet 30.

Front core part 29 is provided with step 292 that faces step 581 of axis fixing part 58 on the outer periphery side of yoke peripheral wall 522 disposed on the outer periphery of coil 21. Elastic body 70D disposed on the outer periphery side of yoke peripheral wall 522 is interposed between step 292 of front core part 29 and step 581 of axis fixing part 58.

One end 71D (see FIG. 11) of both ends of elastic body 70 in the coil-winding axis CL direction is fixed to step 292, and the other end 72D of the both ends of elastic body 70 in the coil-winding axis CL direction is fixed to step 581 of axis fixing part 58.

In linear actuator 10D, movable member 50D is supported with respect to fixing body 40D by elastic body 70D disposed on the outer periphery side of the magnetic circuit at the other end 72D in the coil-winding axis CL direction.

Elastic body 70D is composed of a coil spring, and has an internal diameter greater than the outer diameter of yoke 52D that is disposed on the outer periphery side of coil 21 such that it is movable in the coil-winding axis CL direction. In elastic body 70D, that is, in the coil spring, coil 21 and yoke 52D (yoke peripheral wall 522) that is disposed on the outer periphery side of coil 21 such that it is movable in the coil-winding axis CL direction are disposed.

Bobbin 23D is formed of a non-magnetic substance, and is provided with flanges at both end portions of the cylindrical body, and coil 21 is wound on the outer periphery of the body with the winding axis of coil 21 serving as the central axis of bobbin 23D. It is to be noted that, regarding the flanges of bobbin 23D, the flange which is joined to front core part 29 has a greater outer diameter relative to the other.

The coil winding of coil 21 is connected with a substrate not illustrated, and connected with an external terminal through the substrate. Coil 21 is connected with alternating-current supplying section 80 (see FIG. 12) through the external terminal.

In linear actuator 10D, movable member 50D is supported with respect to fixing body 40D by elastic body 70D disposed along coil-winding axis CL on the outer periphery side of yoke 52D of movable member 50D such that movable member 50D can reciprocate along the coil-winding axis CL direction.

According to the present embodiment, a coil spring is adopted as elastic body 70D that supports movable member 50D such that movable member 50D can linearly reciprocate, and coil spring is disposed on outer side of yoke 52D. With this configuration, an effect similar to that of actuator 10 of Embodiment 1 can be obtained, and the total length of linear actuator 10D itself can be shortened.

Embodiment 6

Figure 14:
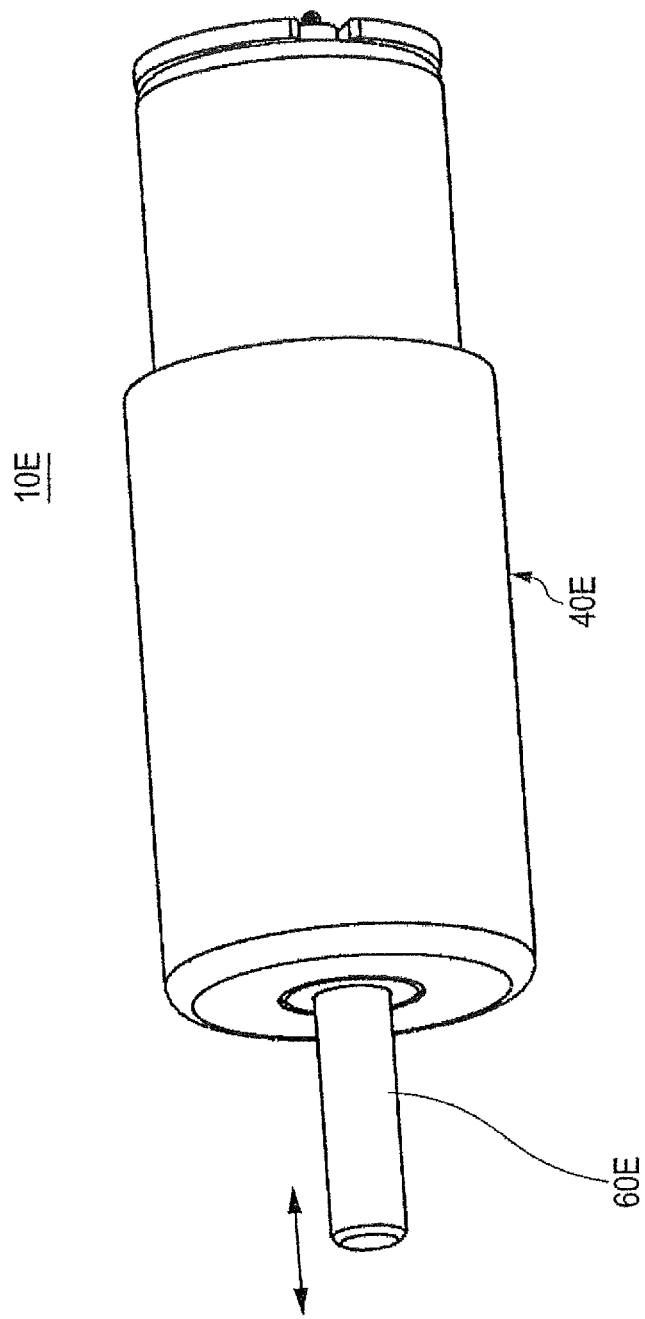
FIG. 14 is an external appearance view illustrating a linear actuator according to Embodiment 6 of the present invention.
Figure 15:
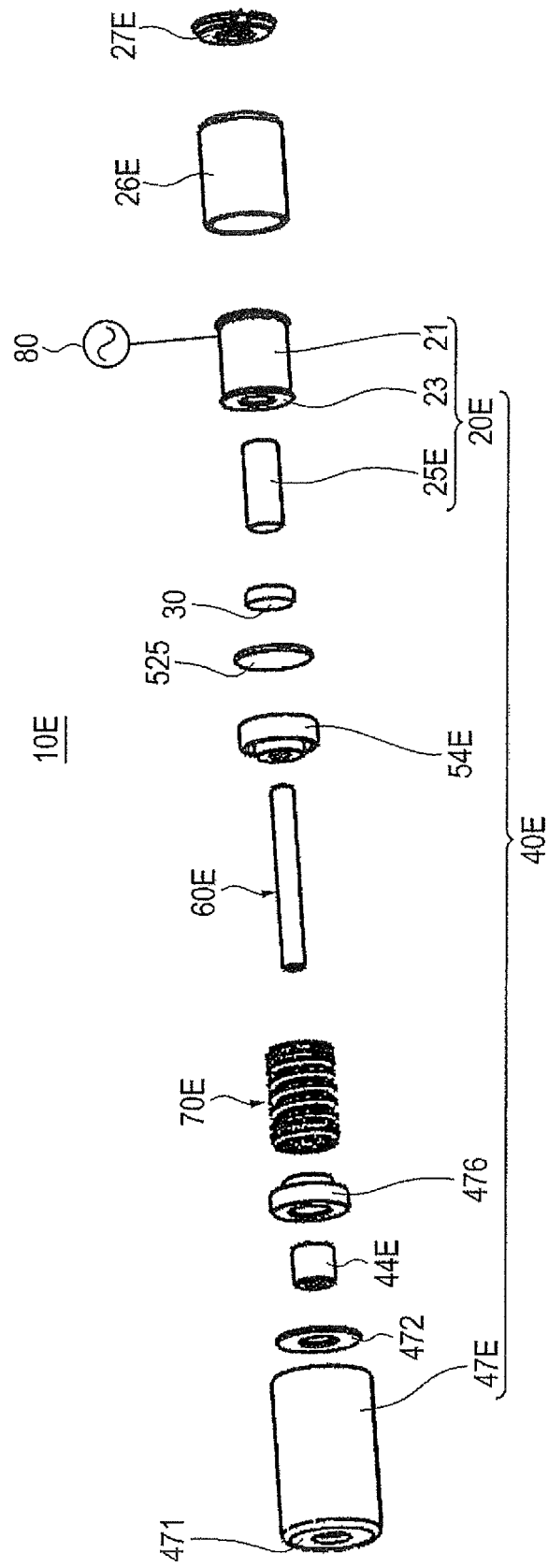
FIG. 15 is an exploded perspective view of the linear actuator according to Embodiment 6 of the present invention.
Figure 16:
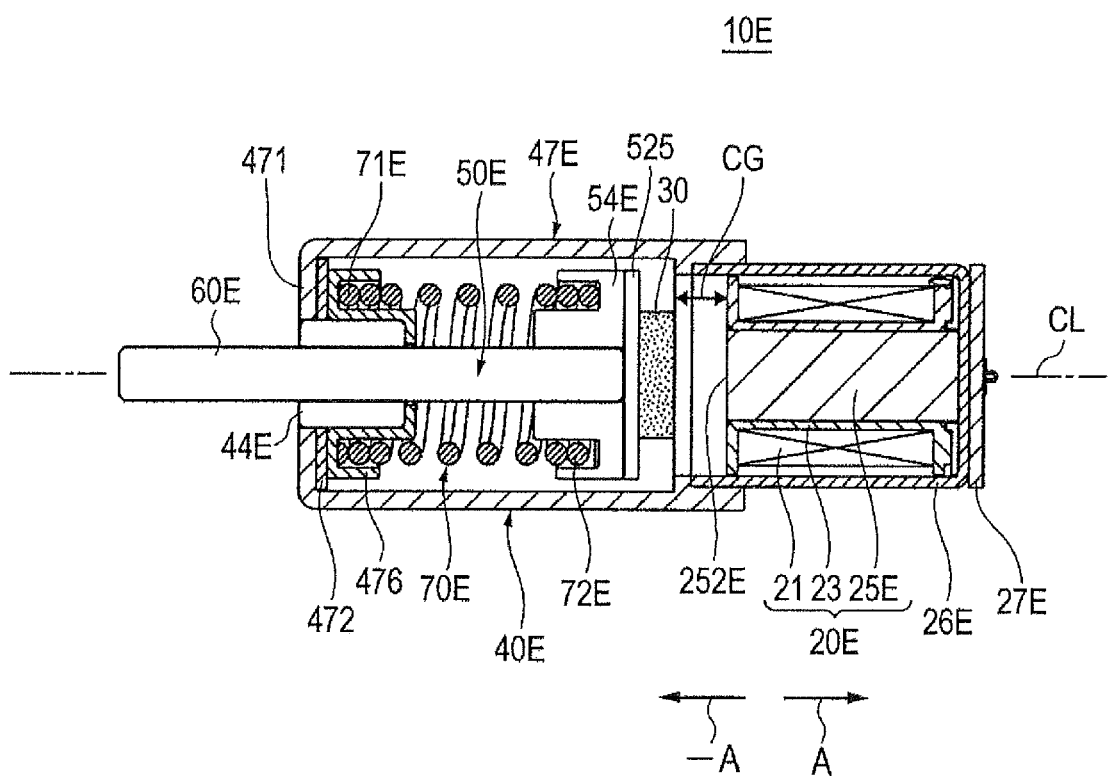
FIG. 16 is a schematic sectional view of a configuration of a main part of the linear actuator according to Embodiment 6 of the present invention.

FIG. 14 is an external appearance view illustrating linear actuator 10E according to Embodiment 6 of the present invention, and FIG. 15 is an exploded perspective view of linear actuator 10E. FIG. 16 is a schematic sectional view illustrating a configuration of a main part of linear actuator 10E.

It is to be noted that linear actuator 10E has a basic configuration similar to that of linear actuator 10 of Embodiment 1 illustrated in FIGS. 1 to 3, and therefore the same components are denoted by the same reference numerals, and the description thereof will be omitted.

In the configuration of the magnetic circuit of actuator 10 of Embodiment 1, linear actuator 10E of Embodiment 6 has a configuration in which output shaft 60E of the movable member including magnet 30 disposed to face coil 21 in the coil-winding axis CL (see FIG. 16) direction, and bearing 44E are provided on the side opposite to coil 21 side.

That is, in linear actuator 10E, magnet 30 is disposed to face coil 21 of electromagnet 20E with a predetermined gap (central air gap CG) therebetween in the coil-winding axis CL direction of coil 21 such that magnet 30 is movable in the coil-winding axis CL direction. It is to be noted that, in linear actuator 10E, coil-winding axis CL of coil 21, the axis of output shaft 60E, the central axis of magnet 30, and the central axis of elastic body 70 are aligned or substantially aligned as axis CL. In this case, the components are disposed such that the axes are aligned along the same line. In addition, magnet 30 is disposed such that it is magnetized in a unipolar fashion along the axial direction.

To be more specific, linear actuator 10E includes fixing body 40E having electromagnet 20E, movable member 50E having magnet 30 and output shaft 60E, and elastic body 70E that supports movable member 50E in fixing body 40E such that movable member 50E is movable in the axis (CL) direction of output shaft 60E.

Fixing body 40E includes electromagnet 20E, cylindrical case 47E, core member 29E, bearing 44E, and fixing side spring receiving part 476.

Case 47E is formed of a non-magnetic substance such as aluminum, and has a capped cylindrical shape that is provided with, at one end of the at the cylindrical part, closure 471 on the front side that has a hole at its center. In this case, case 47E is disposed such that its opening of the cylindrical part faces the rear side.

In case 47E, annular spacer 472 is disposed on the rear surface of annular closure 471, and bearing 44E is inserted to the center portion of closure 471 and spacer 472. In case 47E, fixing side spring receiving part 476 having an opening at its center portion is disposed on the rear side of bearing 44E and spacer 472. Movable member 50E is disposed on the other end 72E side of elastic body 70E through elastic body 70E fixed to fixing side spring receiving part 476 at its one end 71E.

Cylindrical core 26E in which electromagnet 20E is housed is fixed to the opening end that opens to the rear side of case 47E such that electromagnet 20E faces magnet 30 disposed in case 47E in the state where the internal space of case 47E is ensured.

Electromagnet 20E has a configuration similar to that of Embodiment 1. Coil 21 is wound on the external surface of the cylindrical body of bobbin 23 that is formed of a non-magnetic substance, and columnar main body core 25E that is formed of a magnetic substance is inserted in the body.

Bottomed cylindrical core 26E is formed of a magnetic substance, and plate core 27E that is formed of a magnetic substance is fixed on the rear surface of the bottom surface. In cylindrical core 26E, electromagnet 20E is disposed along the coil-winding axis CL.

In addition, main body core 25E of electromagnet 20E is joined to a center portion of the bottom of cylindrical core 26E. With this configuration, main body core 25E serves as a core having an E-shape in cross-section together with cylindrical core 26E. It is to be noted that the central axis of main body core 25E, the coil-winding axis of coil 21, and the central axis of cylindrical core 26E are aligned along the same axis. This axis is illustrated as coil-winding axis CL in FIG. 16. The coil winding of coil 21 is connected with a substrate not illustrated, and is connected with an external terminal through the substrate. Alternating current power (alternating current voltage) is supplied to coil 21 from alternating-current supplying section 80 through the external terminal.

In the state where electromagnet 20E is mounted therein, the opening end of cylindrical core 26E is fixed to the opening end of case 47E.

One end surface 252E of electromagnet 20E of cylindrical core 26E is exposed to the interior of case 47E, and faces magnet 30 of movable member 50E disposed in case 47E with a predetermined gap (central air gap CG) therebetween.

Magnet 30 is fixed to one surface of disk-shaped plate yoke 525 that is formed of a magnetic substance disposed orthogonal to the coil-winding axis. Movable side spring receiving part 54E is fixed on the surface of plate yoke 525 opposite to the surface on which magnet 30 is fixed. Movable side spring receiving part 54E is disposed to face fixing side spring receiving part 476, and is joined to fixing side spring receiving part 476 through elastic body 70.

Together with fixing side spring receiving part 476, movable side spring receiving part 54E is formed in a protruding shape in cross section, and the protrusions are inserted to the inside from the both ends of the coil spring serving as elastic body 70E such that movable side spring receiving part 54E is fixed at its position and that the axes of fixing side spring receiving part 476 and movable side spring receiving part 54E are aligned.

Output shaft 60E protrudes toward one end 71E of the coil spring serving as elastic body 70E at the center of movable side spring receiving part 54E, and output shaft 60E extends through the inside of elastic body 70E, fixing side spring receiving part 476, and bearing 44E and protrudes outward from closure 471.

In this configuration, when alternating current power is supplied to coil 21 from alternating-current supplying section 80 (see FIG. 15), one end surface of main body core 25E serving as one end surface 252E is excited to have a polarity, and thus the surface attracts or repulses magnet 30 that faces thereto.

As with Embodiment 1, when power is supplied to coil 21 from alternating-current supplying section 80 as with actuator 10, movable member 50E reciprocates in the axis CL direction with respect to fixing body 40E, and along with this reciprocation, output shaft 60E reciprocates in the axis CL direction (thrust A direction and −A direction), whereby the reciprocation is output to the outside. With this configuration, an effect similar to that of linear actuator 10 of Embodiment 1 can be achieved, and in comparison with linear actuator 10, it is possible to use the space occupied by output shaft 60E and bearing 44E in the magnetic circuit in linear actuator 10E. Consequently, energy conversion efficiency in linear actuator 10E can be enhanced, and thus downsizing can be achieved.

Embodiment 7

Figure 17:
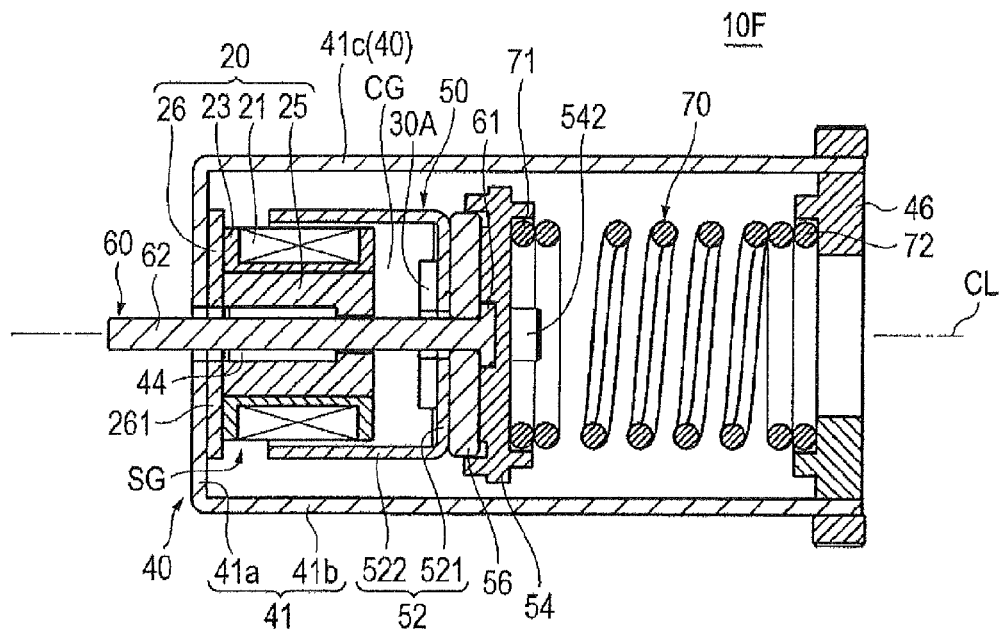
FIG. 17 is a schematic sectional view illustrating a configuration of a main part in a linear actuator according to Embodiment 7 of the present invention.
Figure 18:
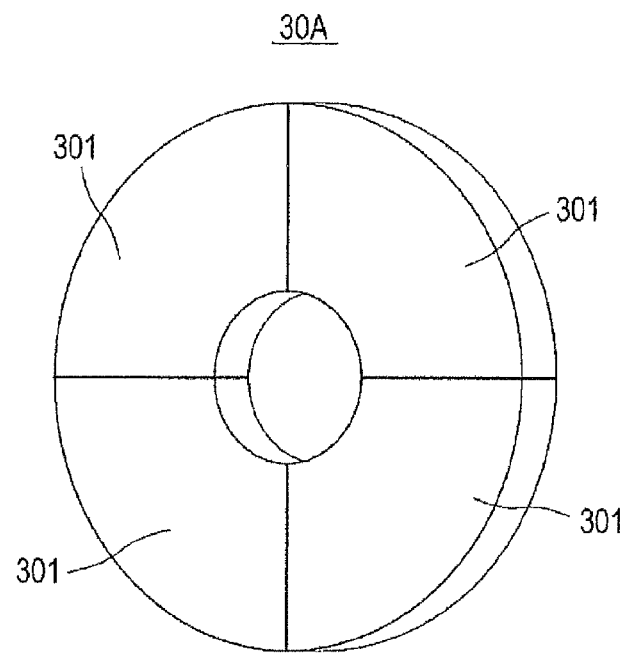
FIG. 18 is a perspective view illustrating a magnet of the linear actuator according to Embodiment 7 of the present invention.

FIG. 17 is a schematic sectional view illustrating a configuration of a main part of a linear actuator according to Embodiment 7 of the present invention, and FIG. 18 is a perspective view illustrating a magnet of the linear actuator according to Embodiment 7 of the present invention. Linear actuator 10F illustrated in FIG. 17 differs from linear actuator 10 of Embodiment 1 illustrated in FIGS. 1 to 4 in that magnet 30A is adopted in place of magnet 30, and other configurations are the same as those of linear actuator 10. Therefore, the same components are denoted by the same reference numerals, and the description thereof will be omitted. Specifically, as with the configuration of linear actuator 10, in linear actuator 10F illustrated in FIG. 17, fixing body 40 has electromagnet 20 having coil 21. Movable member 50 faces coil 21 in the winding axis CL direction of coil 21, and includes magnet 30A magnetized in a unipolar fashion in the coil-winding axis CL direction and output shaft 60 extending in the CL direction. Elastic body 70 is fixed to fixing body 40 and movable member 50 at both ends 71 and 72 in the coil-winding axis CL direction, respectively, such that central air gap CG is formed between electromagnet 20 and magnet 30A. Movable member 50 reciprocates with respect to fixing body 40 in the axis CL direction with power supplied from alternating-current supplying section 80 (omitted in the drawing), and along with this reciprocation, output shaft 60 reciprocates along the axis CL direction (arrow direction), whereby the reciprocation is output to the outside.

As illustrated in FIG. 18, magnet 30A in linear actuator 10F is composed of a plurality of separated magnets 301 which are obtained by dividing magnet 30A. Separated magnets 301 are obtained by dividing magnet 30A in a direction along output shaft 60 (which corresponds to coil-winding axis CL). Separated magnets 301 have the same shape. Separated magnets 301 having the same shape and the same magnetization direction are disposed in a circle about output shaft 60 to obtain annular magnet 30A. While magnet 30A is composed of four separated magnets 301 in FIG. 18, the number of the magnets is not limited as long as two or more magnets 301 are used.

With linear actuator 10F, an effect similar to that of linear actuator 10 can be achieved, and magnet 30A can be easily attached to yoke 52 without insertion of output shaft 60. In addition, since separated magnets 301 have the same shape, the magnets can be easily incorporated by only aligning the magnetization directions even when the magnets are incorporated at the position around output shaft 60 with respect to bottom surface 521 of yoke 52. It is to be noted that magnet 30A composed of separated magnets 301 may be adopted in place of magnet 30 of linear actuators 10A, 10B, 10C, 10D and 10E of Embodiments 2 to 6. The operation and effect obtained when magnet 30A is used in actuators 10A, 10B, 10C, 10D and 10E are the same as those of magnet 30A in Embodiment 7, and therefore the description thereof will be omitted.

It is to be noted that linear actuators 10A to 10F of Embodiments 2 to 7 are driven based on Expressions 1, 2 and 3 as with linear actuator 10. That is, when the mass of movable member (50A to 50E) is represented by m [Kg], and the spring constant of elastic body (70, 70D and 70E) in the coil-winding axis direction is represented by $K_{s\,p}$ in linear actuators 10A to 10F, the movable member vibrates with respect to fixing body (40A to 40E) with resonance frequency $f_0$ [Hz] calculated based on the above-mentioned Expression 1. In linear actuators 10A to 10F, alternating-current supplying section 80 supplies coil 21 with an alternating current having a frequency substantially equal to resonance frequency $f_0$ [Hz] of the movable member. With this configuration, the movable members can be driven in a resonance state to provide a high output, with high efficiency. In addition, linear actuators 10A to 10E are driven based on the equation of motion of Expression 2 and the circuit equation of Expression 3 as with linear actuator 10.

In linear actuators 10A to 10E of Embodiments 2 to 7, elastic bodies 70, 70D and 70E are disposed along the coil-winding axis CL direction, and are elastically deformed in the coil-winding axis CL direction to support movable members 50A to 50E in fixing body 40A to 40E such that movable members 50A to 50E can reciprocate along the coil-winding axis CL direction. Elastic bodies 70, 70D and 70E are respectively fixed to fixing bodies 40A to 40E and movable members 50A to 50E at respective both end portions 71, 71D, 71E, 72, 72D and 72E in the coil-winding axis CL direction such that central air gap CG is formed between electromagnet 20, 20C, 20D or 20E and magnet 30 or 30A. With linear actuators 10A to 10F, it is possible to achieve simple configuration, downsizing, and stable linear reciprocation while achieving improvement in assemblability and cost reduction.

It is to be noted that, in linear actuators 10A to 10F of Embodiments 2 to 7, the central axis of the elastic body, the coil-winding axis of coil 21, the axis of the output shaft, and the central axes of magnets 30 and 30A are aligned or substantially aligned as axis CL. In each embodiment, the elastic body, coil, bobbin, output shaft, magnet and the like are disposed such that the axes are aligned along the same axis.

In addition, when bearings 44 and 44D are formed of a magnetic substance, energy conversion efficiency can be enhanced without wasting the magnetic flux generated by magnet 30, and further, actuators 10 and 10A to 10D can be downsized.

In addition, since output shafts 60 and 60D are formed of a non-magnetic substance in each embodiment, unnecessary attraction force is not exerted on output shafts 60 to 60D at the time of assembling. With this configuration, assemblability can be improved and the magnetic flux of magnets 30 and 30A is not wasted. Consequently, energy conversion efficiency can be enhanced and the actuator can be downsized.

While magnet 30 of linear actuators 10 to 10E in the embodiments is single one, a plurality of magnets 30 may be adopted and disposed as one unipolar magnet as with the magnet of Embodiments 1 to 6 so as to have a function same as that in Embodiments 1 to 6.

In addition, linear actuators 10, 10A, 10B, 10C, 10D, 10E and 10F of the embodiments may be appropriately employed in electric brushes, electric cutting machines and electric air pumps.

In the following, as an example of electric brushes, electric cutting machines and electric air pumps having linear actuator 10, 10A, 10B, 10C, 10D, 10E or 10F, an electric brush, an electric cutting machine and an electric air pump having the main configuration of linear actuator 10E are described.

<Outline of Configuration of Electric Toothbrush>

Figure 19:
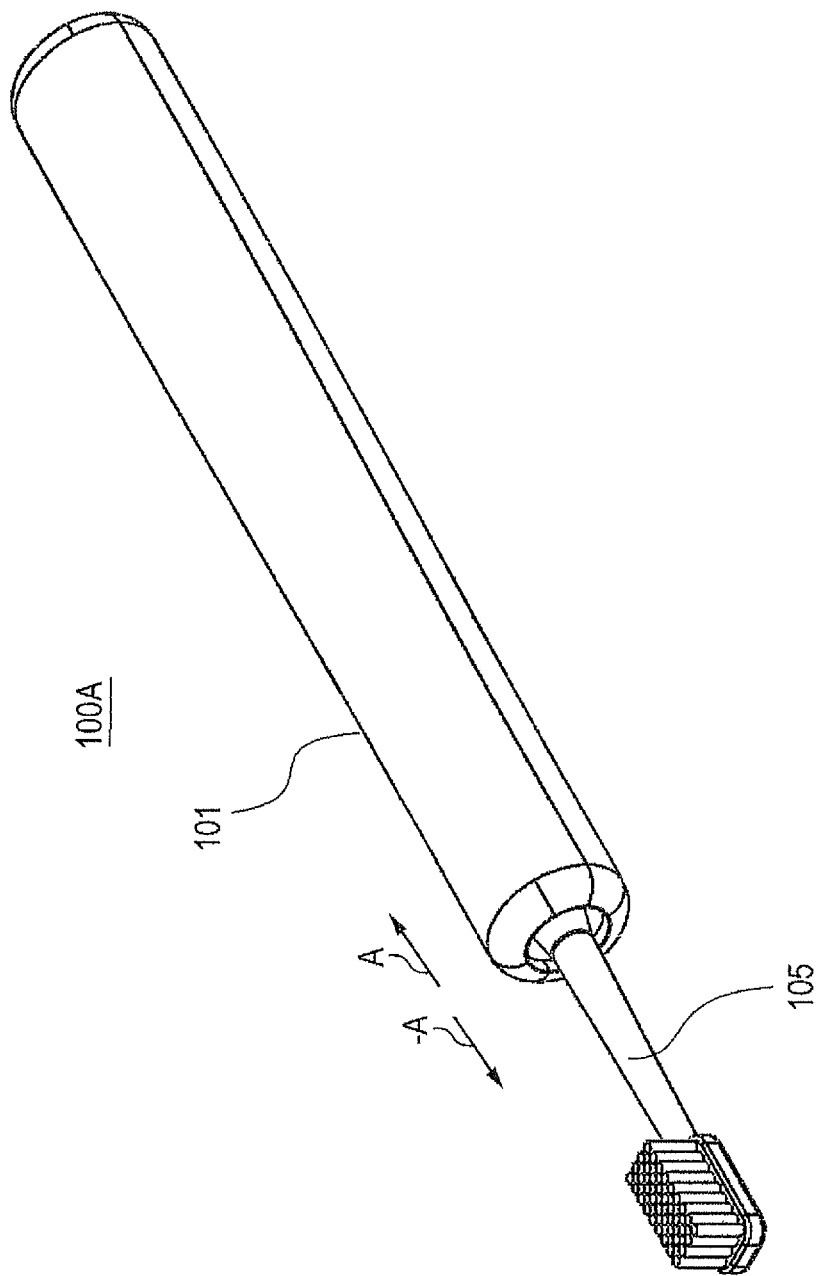
FIG. 19 is a perspective view illustrating an electric toothbrush including the linear actuator of the embodiments of the present invention.
Figure 20:
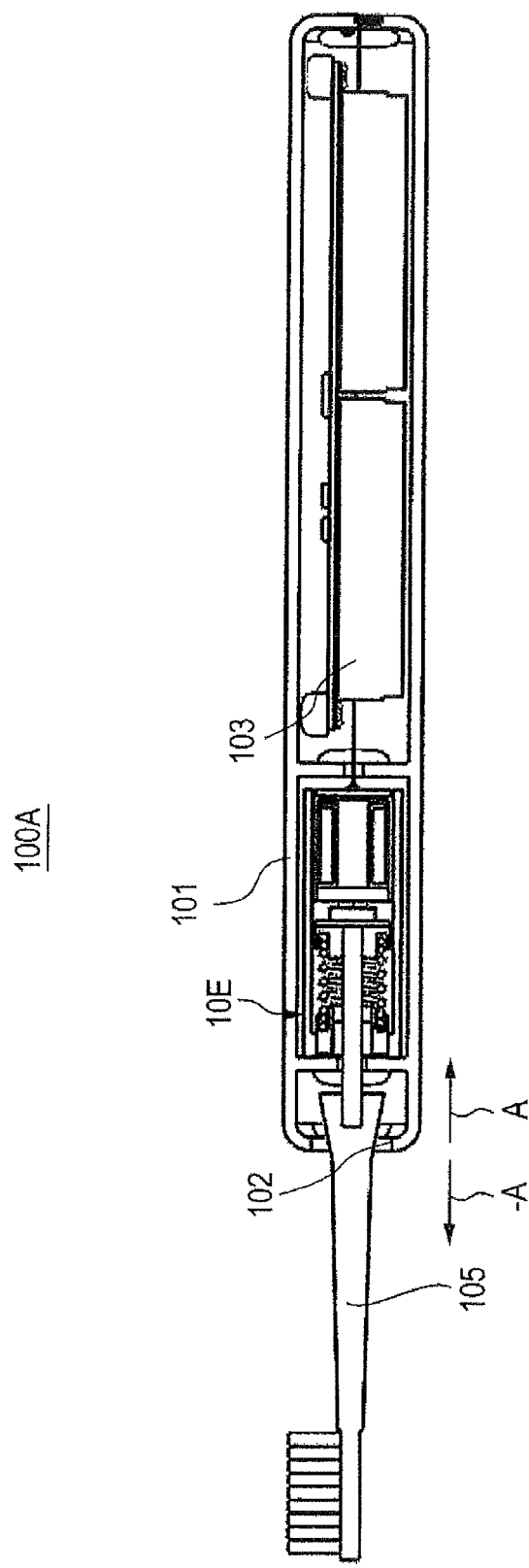
FIG. 20 is a schematic sectional view illustrating a configuration of a main part of the electric toothbrush.

FIG. 19 is a perspective view illustrating an electric toothbrush including the linear actuator according to Embodiment 6 of the present invention, and FIG. 20 is a longitudinal sectional view illustrating a configuration of a main part of the electric toothbrush.

Electric toothbrush 100A illustrated in FIG. 19 and FIG. 20 includes toothbrush part 105, cylindrical (shaft-shaped) housing 101, and battery 103 and linear actuator 10E disposed in housing 101.

Housing 101 has a shape extending in the longitudinal direction, and has at its one end opening part 102 to which toothbrush part 105 is inserted.

The base end of toothbrush part 105 to be inserted from opening part 102 is detachably attached with its axis aligned with output shaft 60E of linear actuator 10E.

Linear actuator 10E is disposed in housing 101 such that the axis of output shaft 60E (winding axis CL of coil 21 illustrated in FIG. 16) is set along the longitudinal direction of housing 101. In addition, linear actuator 10E is connected with batteries 103 disposed side by side along the direction of the axis of output shaft 60E (winding axis CL of coil 21) (longitudinal direction) in housing 101. Batteries 103 are a part of the alternating-current supplying section (omitted in the drawing), and an alternating current is supplied to linear actuator 10E (to be more specific, coil 21 illustrated in FIG. 16) from the alternating-current supplying section. With this configuration, linear actuator 10E moves output shaft 60E in the arrow direction (A direction and −A direction) with the power from the battery, and consequently, toothbrush part 105 is reciprocated.

As described, with the small sized configuration, linear actuator 10E can be disposed in shaft-shaped slender housing 101 to move toothbrush part 105.

<Outline of Configuration of Electric Cutting Machine>

Figure 21:
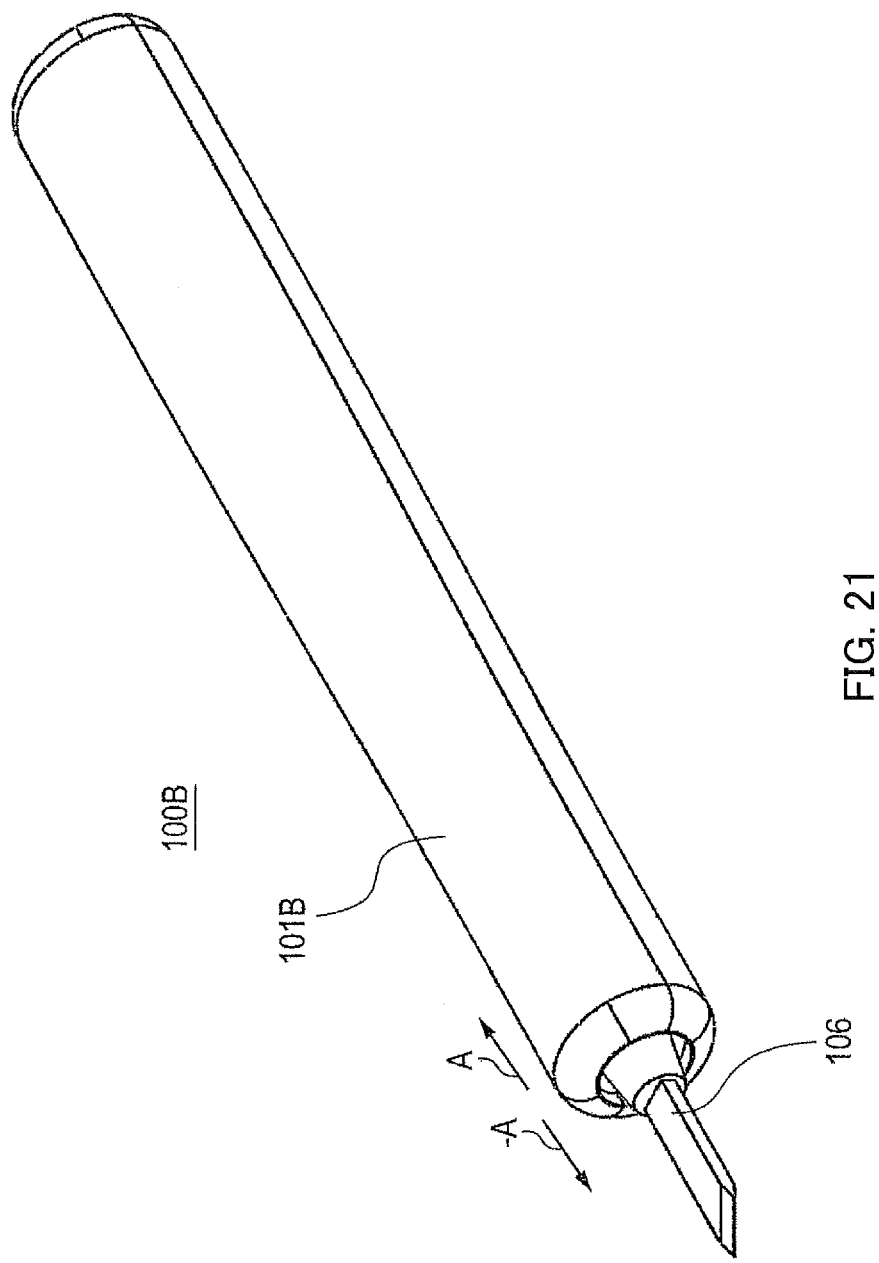
FIG. 21 is a perspective view illustrating an electric cutting machine including the linear actuator of the embodiments of the present invention.
Figure 22:
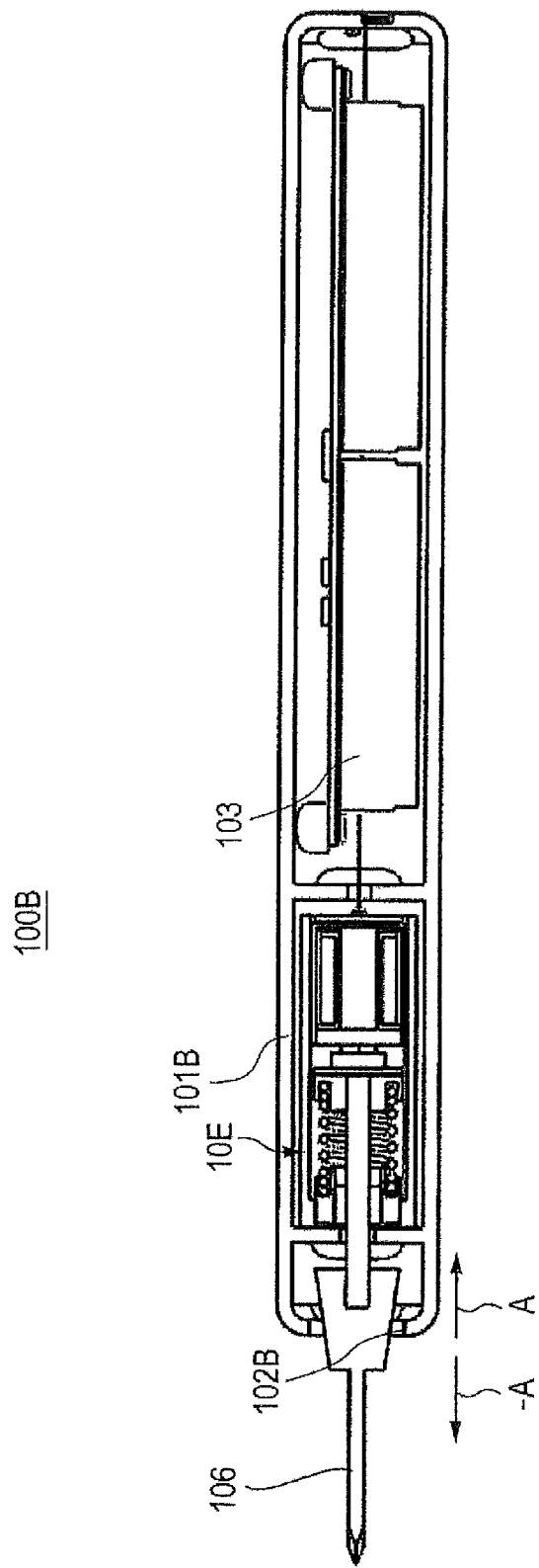
FIG. 22 is a schematic sectional view illustrating a configuration of a main part of the electric cutting machine.

FIG. 21 is a perspective view illustrating an electric cutting machine having the linear actuator according to Embodiment 6 of the present invention, and FIG. 22 is a longitudinal sectional view illustrating a configuration of a main part of the electric cutting machine.

In electric cutting machine 100B illustrated in FIG. 21 and FIG. 22, cutting part (cutting blade) 106 is attached to output shaft 60E in place of toothbrush part 105 as the attachment in the configuration of electric toothbrush 100A illustrated in FIG. 19 and FIG. 20. Specifically, electric cutting machine 100B includes cutting part 106, cylindrical (shaft-shaped) housing 101B, battery 103, and linear actuator 10E.

Cutting part 106 has a blade at an end thereof. Housing 101B has a shape extending in the longitudinal direction, and the base end of cutting part 106 is inserted to opening part 102B formed at an end of housing 101B. The base end of cutting part 106 inserted from opening part 102 is detachably attached with its axis aligned with output shaft 60E of linear actuator 10E.

Linear actuator 10E is disposed in housing 101B such that the axis of output shaft 60E (winding axis CL of coil 21) is aligned along the longitudinal direction of housing 101B. In addition, linear actuator 10E is connected with batteries 103 disposed side by side along the direction of the axis of output shaft 60E (winding axis CL of coil 21) (longitudinal direction of housing 101B) in housing 101B. Batteries 103 are a part of the alternating-current supplying section (omitted in the drawing), and an alternating current is supplied to linear actuator 10E (to be more specific, coil 21 illustrated in FIG. 16) from the alternating-current supplying section. With this configuration, linear actuator 10E moves output shaft 60E in the arrow direction (A direction and −A direction) with the power from the battery, and consequently, cutting part 106 is reciprocated. As described, with the small sized configuration, linear actuator 10E can be disposed in shaft-shaped slender housing 101B to move cutting part 106.

<Outline of Configuration of Electric Air Pump>

Figure 23:
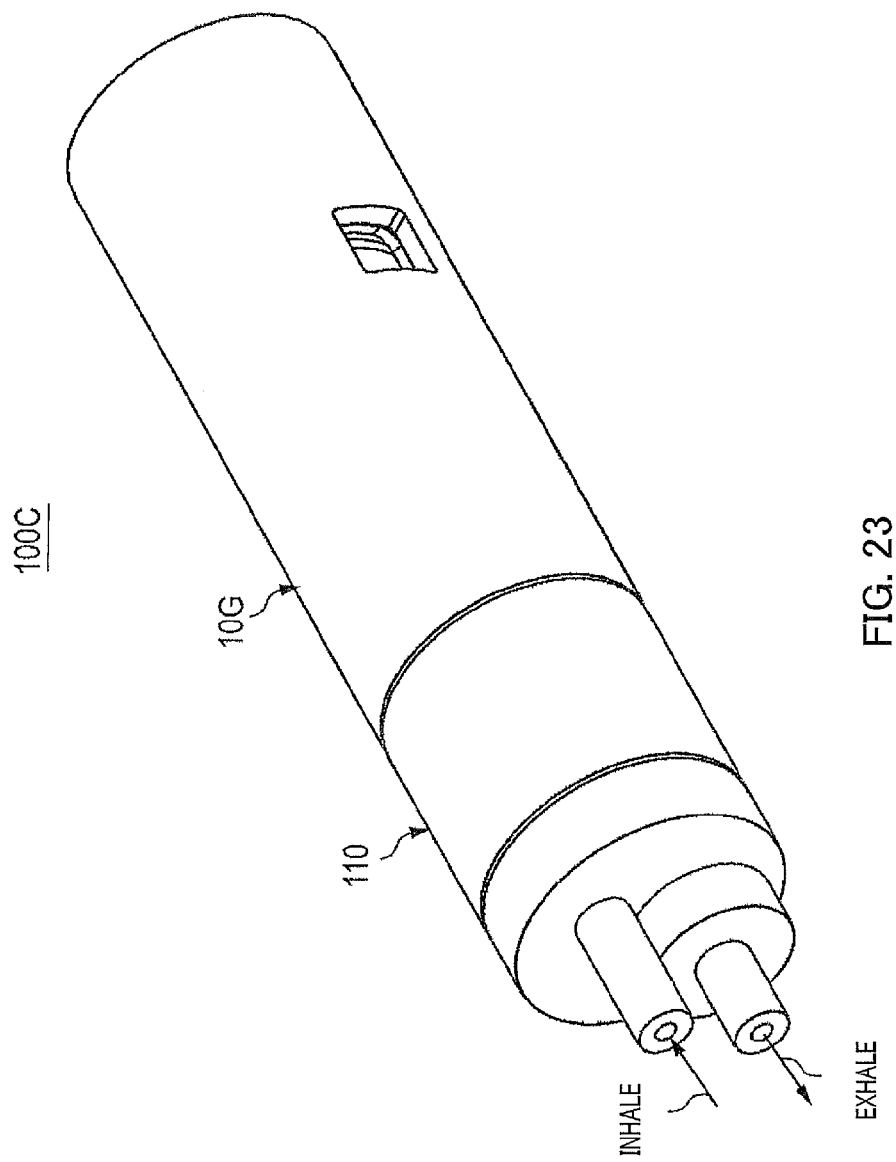
FIG. 23 is a perspective view illustrating an electric air pump including the linear actuator of the embodiments of the present invention.
Figure 24:
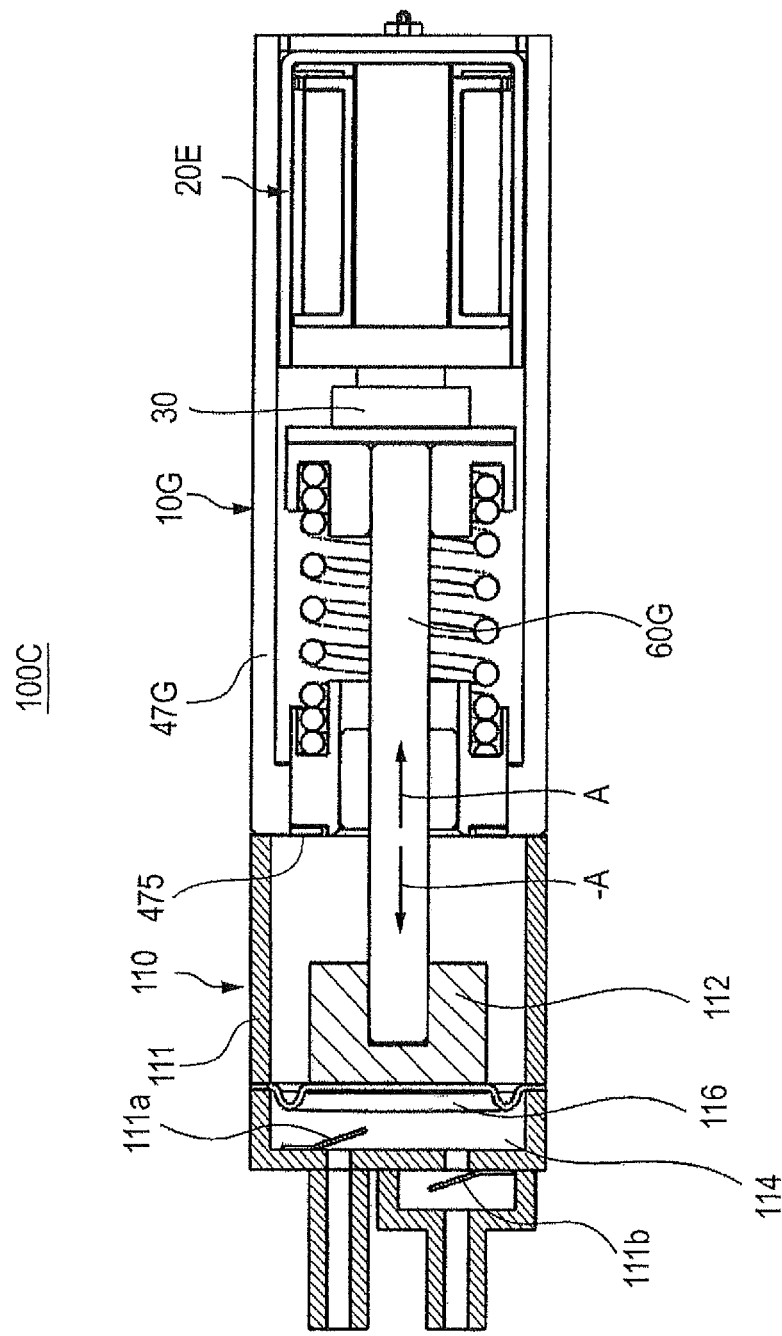
FIG. 24 is a schematic sectional view illustrating a configuration of a main part of the electric air pump.

FIG. 23 is a perspective view illustrating an electric air pump including the linear actuator according to Embodiment 6 of the present invention, and FIG. 24 is a schematic sectional view illustrating a configuration of a main part of the electric air pump.

Electric air pump 100C illustrated in FIG. 23 and FIG. 24 includes linear actuator 10G, and pump unit 110 joined to one end surface 475 (output side surface) of linear actuator 10G.

It is to be noted that, in linear actuator 10G in electric air pump 100C, pump case 47G that houses electromagnet 20E together with movable member 50E is adopted in place of case 47E in the configuration of linear actuator 10E illustrated in FIG. 16. Other basic configurations are similar to those of linear actuator 10E, and the operation and effect of the magnetic circuit are basically similar to those of linear actuators 10, 10A to 10D and 10F. Therefore, the same names and reference numerals are given to the components similar to those of linear actuator 10E, and description thereof are omitted. Linear actuator 10G includes a magnetic circuit similar to that of linear actuator 10E, and has output shaft 60G that is reciprocated by the magnetic circuit in the axial direction.

Output shaft 60G is disposed to protrude from one end surface 475 side (a side opposite to electromagnet 20E with magnet 30 therebetween) of pump case 47G, and is joined to plunger 112 in pump unit 110.

Pump unit 110 includes inhalation valve 111a, case 111 provided with exhaust valve 111b, diaphragm part 116 that forms pump chamber 114 in case 111, and plunger 112 that moves diaphragm part 116 in the axial direction. It is to be noted that plunger 112 is fixed to diaphragm part 116 on the side opposite to pump chamber 114.

Specifically, in pump unit 110, along with the movement of output shaft 60G of plunger 112 joined to output shaft 60G, diaphragm part 116 moves in the axial direction in case 111. With the movement of diaphragm part 116 in the axial direction, pump chamber 114 expands and contracts such that air intake and exhaust to and from pump chamber 114 are performed through inhalation valve 111a and exhaust valve 111b. That is, when linear actuator 10G is driven, output shaft 60G reciprocates in the arrow direction (A direction and −A direction), and consequently, through plunger 112, the air is input or output to or from pump chamber 114 through inhalation valve 111a and exhaust valve 111b. Since linear actuator 10G has a small-sized configuration, electric air pump 100C can be formed in a slender cylindrical shape in its entirety.

While the invention made by the present inventor has been specifically described based on the preferred embodiments, it is not intended to limit the present invention to the above-mentioned preferred embodiments but the present invention may be further modified within the scope and spirit of the invention defined by the appended claims.

INDUSTRIAL APPLICABILITY

The linear actuator according to the embodiments of the present invention can achieve downsizing with a simple configuration, and can provide stable linear reciprocation while achieving improvement in assemblability and cost reduction. The linear actuator according to the embodiments of the present invention can be employed in small-sized slender electric brushes and electric cutting machines and small-shaped electric air pumps.

REFERENCE SIGNS LIST 10, 10A, 10B, 10C, 10D, 10E, 10F, 10G Linear actuator
20, 20C, 20D, 20E Electromagnet
21 Coil
23, 23D Bobbin
24E Core
25, 25E Main body core
26, 27E Plate core
26C Disk core
26E Cylindrical core
28 Magnetic case
29 Front core part
30, 30A Magnet
32 Opposing surface
40, 40A, 40B, 40C, 40D, 40E Fixing body
41 Baseplate
41a Front plate part
41b, 41c Side plate part
44, 44D, 44E Bearing
46, 48 Spring receiving part
47, 47E Case
50, 50A, 50B, 50C, 50D, 50E Movable member
52, 52D Yoke
54, 54E Movable side spring receiving part
55, 525 Plate yoke
56 Bonding plate
57 Cup-shaped magnetic substance
58 Axis fixing part
60, 60D, 60E Output shaft
61 Flange
62 Shaft
70, 70D, 70E Elastic body
71, 71D, 71E One end
72, 72D, 72E Other end
80 Alternating-current supplying section
252, 252E Main body core end surface
301 Separated magnets
471 Closure
472 Spacer
474 Movable side spring receiving part
476 Fixing side spring receiving part
521 Yoke bottom surface
522 Yoke peripheral wall
CG Central air gap (air gap)

The invention claimed is:

1. A linear actuator comprising:
an electromagnet including a coil and comprising an end surface at an end of the electromagnet in a coil-winding axis direction of the coil;
a magnet comprising a unipolar, magnetized surface disposed at an end of the magnet to be spaced from the end surface of the electromagnet in the coil-winding axis direction and face the end surface of the electromagnet;
a movable member including one of the electromagnet and the magnet and including an output shaft extending in the coil-winding axis direction;
a fixing body including the other of the electromagnet and the magnet;
an elastic body disposed along the coil-winding axis direction and configured to elastically deform in the coil-winding axis direction to support the movable member such that the movable member is allowed to reciprocate in the coil-winding axis direction; and
an alternating-current supplying section configured to supply an alternating current having a frequency substantially equal to a resonance frequency of the movable member to the coil, wherein
both end portions of the elastic body in the coil-winding axis direction are fixed to the fixing body and to the movable member respectively such that an air gap is formed between the end surface of the electromagnet and the unipolar, magnetized surface of the magnet.

2. The linear actuator according to claim 1, wherein the elastic body is composed of a coil spring that expands and contracts in the coil-winding axis direction.

3. The linear actuator according to claim 2, wherein the coil spring of the elastic body is wound to surround the electromagnet and the magnet.

4. The linear actuator according to claim 1, wherein:
the movable member includes the magnet;
the fixing body includes the electromagnet;
the electromagnet includes a main body core that is formed of a magnetic substance provided in the coil; and
the main body core is provided with a bearing through which the output shaft of the movable member is inserted such that the output shaft is movable in the coil-winding axis direction.

5. The linear actuator according to claim 4, wherein the bearing is formed of a magnetic substance.

6. The linear actuator according to claim 1, wherein:
the movable member includes the magnet and a yoke to which the magnet is fixed; and
the yoke is formed as a bottomed cylinder in which the magnet is fixed on a bottom surface thereof, and a cylinder part of the bottomed cylinder which extends from the bottom surface is disposed to be movable in the coil-winding axis direction such that the cylinder part opens to the electromagnet side of the fixing body and surrounds the coil of the electromagnet from an outer periphery side of the coil of the electromagnet.

7. The linear actuator according to claim 1, wherein:
the movable member includes the magnet and a yoke having a disk shape to which the magnet is fixed at a center thereof;
the fixing body includes the electromagnet;

the electromagnet includes a main body core that is formed of a magnetic substance provided in the coil, and is mounted in a bottomed cylindrical core that is formed of a magnetic substance with a central axis of the bottomed cylindrical core aligned along the coil-winding axis direction;

the main body core is integrally joined to an internal bottom surface of the bottomed cylindrical core; and an opening end of the bottomed cylindrical core faces toward the yoke having the disk shape such that the main body core and the magnet face each other with the air gap therebetween.

8. The linear actuator according to claim 1, wherein:

the electromagnet includes a main body core that is formed of a magnetic substance and provided in the coil-winding axis direction in the coil;

the fixing body includes the electromagnet and a bottomed cylindrical core, the bottomed cylindrical core being formed of a magnetic substance and having a bottomed cylindrical shape in which the electromagnet is disposed and the main body core is joined on a bottom surface thereof;

the movable member includes the magnet and a yoke having a bottomed cylindrical shape in which the magnet is fixed on a bottom surface thereof;

the electromagnet is disposed in the bottomed cylindrical core such that the coil-winding axis of the electromagnet is set along a central axis of the bottomed cylindrical core; and the bottomed cylindrical core and the yoke have a same shape and are disposed such that an opening end of the bottomed cylindrical core and an opening end of the yoke face each other.

9. The linear actuator according to claim 1, wherein the magnet is composed of a neodymium magnet.

10. The linear actuator according to claim 1, wherein the magnet is composed of a plurality of similarly formed magnets which are disposed in a circle about the output shaft and have a same magnetization direction.

11. The linear actuator according to claim 1, wherein the output shaft is formed of a non-magnetic substance.

12. The linear actuator according to claim 1, wherein the fixing body includes a case configured to cover the elastic body and the movable member and support the movable member by the elastic body such that the movable member is allowed to reciprocate in the coil-winding axis direction.

13. An electric brush comprising the linear actuator according to claim 1.

14. An electric cutting machine comprising the linear actuator according to claim 1.

15. An electric air pump comprising the linear actuator according to claim 1.

* * * * *